United States Patent [19]

Taylor, Jr.

[11] 4,447,361

[45] May 8, 1984

[54] ARYL SUBSTITUTED PYRIDO[1,4]BENZODIAZEPINES

[75] Inventor: Chandler R. Taylor, Jr., Mechanicsville, Va.

[73] Assignee: A. H. Robins Company, Inc., Richmond, Va.

[21] Appl. No.: 395,218

[22] Filed: Jul. 6, 1982

Related U.S. Application Data

[63] Continuation-in-part of Ser. No. 305,080, Sep. 24, 1981, abandoned.

[51] Int. Cl.³ .................................................. C07D 471/04
[52] U.S. Cl. ............................... 260/244.4; 260/243.3; 424/248.4; 424/248.51; 424/248.58; 424/250; 424/256; 546/261; 546/262; 546/284; 546/307
[58] Field of Search ........................... 260/243.3, 244.4

[56] References Cited

FOREIGN PATENT DOCUMENTS 907646 10/1962 United Kingdom ........ 260/239 DD

OTHER PUBLICATIONS

*Chemical Abstracts*, 79:5388v (1973) [Japan 73 11,110, Ozawa et al., 4/10/73].

*Chemical Abstracts*, 84:164876a (1976) [Japan Kokai No. 76 06,991, Kobayashi et al., 1/20/76].

*Primary Examiner*—Richard A. Schwartz

[57] ABSTRACT

Pyrido[1,4]benzodiazepines having antidepressant activity of the formula

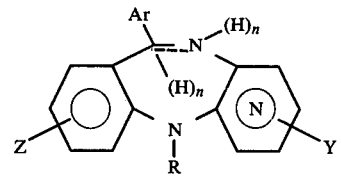

wherein Ar is 2, 3 and 4-pyridinyl, 2 or 3-thienyl, phenyl or a substituted phenyl; R is hydrogen, loweralkyl or an amine on the end of a hydrocarbon chain; Z is hydrogen, halogen, trifluoromethyl, loweralkyl, loweralkoxy, hydroxy or nitro; and Y is hydrogen, loweralkyl, loweralkoxy or hydroxy; and the pharmaceutical salts are prepared from [2-[(aminopyridinyl)amino]-phenyl]arylmethanones which also have antidepressant activity.

34 Claims, No Drawings

ARYL SUBSTITUTED PYRIDO[1,4]BENZODIAZEPINES

This is a continuation-in-part application of application Ser. No. 305,080 filed Sept. 24, 1981, now abandoned.

BACKGROUND OF THE INVENTION

1. Field of Invention

The present invention relates to certain novel pyrido[1,4]benzodiazepines and novel chemical intermediates and pharmaceutical methods and compositions for treating depression in humans.

2. Description of the Prior Art

Wander, A., in British Pat. No. 907,646 dicloses preparation of certain dibenzodiazepines substituted with phenyl radicals on carbon and with alkyl or aminoalkyl radicals on the bridging nitrogen atom between the phenyl rings.

Greig, M. E., et al., J. Med. Chem. 14 No. 2, page 153 (1971), disclose dibenzodiazepines similar to the foregoing Wander disclosure useful against anaphylactic shock.

Japanese Pat. No. 73/43,520 (C.A. 80: 133501n discloses 6-phenyl-2,3,4,4a-tetrahydro-11H-pyrido[2,3-b][1,4]benzodiazepines having anticonvulsant activity which are illustratively prepared from 2-aminobenzophenones and ornithine.

SUMMARY OF THE INVENTION

The novel pyrido[1,4]benzodiazepines of the present invention have the formula

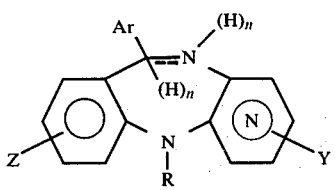

Formula I wherein;

R is selected from the group consisting of hydrogen, loweralkyl, -alk$^1$-halo, -alk$^1$-NR$^1$R$^2$ or -alk$^1$—N=CH—OC$_2$H$_5$;

R$^1$ and R$^2$ are selected from the group consisting of hydrogen, loweralkyl, -C(O)O-loweralkyl, or R$^1$ and R$^2$ taken together with the adjacent nitrogen atom may form a heterocyclic residue selected from the group consisting of 1-piperidinyl, 1-phthalimido, 1-pyrrolidinyl, 4-morpholinyl, 1-piperazinyl, and 4-substituted-1-piperazinyl;

Ar is selected from the group consisting of 2, 3 and 4-pyridinyl, 2 or 3-thienyl, phenyl or phenyl substituted by 1 to 3 radicals selected from halo, loweralkyl, loweralkoxy, trifluoromethyl or nitro and may be the same or different;

Alk$^1$ is a straight or branched hydrocarbon chain containing 1-8 carbon atoms;

Z is selected from the group consisting of hydrogen, halogen, loweralkyl, loweralkoxy, hydroxy or nitro;

Y is selected from the group consisting of hydrogen or 1-2 radicals selected from loweralkyl, loweralkoxy or hydroxy and may be the same or different;

n is 0 and 1 and when n is zero the dotted line is a double bond, and the acid addition salts thereof.

The compounds of Formula I have utility as antidepressants for treating depression or as intermediates in the preparation of other compounds of Formula I.

The novel [2-[(aminopyridinyl)amino]phenyl]arylmethanones and their thioxomethyl, ketal or thioketal analogs which form in the reaction mixture prior to cyclization to diazepines and certain of which have additional utility as antidepressants for treating depression are represented by the formula:

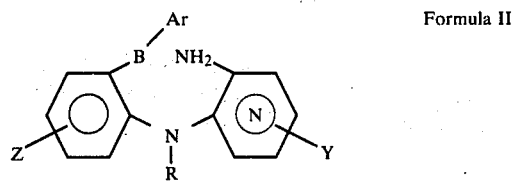

Formula II wherein B is selected from carbonyl, thioxomethyl, ketal or thioketal, and R, R$^1$, R$^2$, Ar, alk$^1$, Z and Y are as defined under Formula I above.

In the further definition of symbols in the formulas hereof and where they appear elsewhere throughout this specification and claims, the terms have the following significance.

The "alk" straight or branched connecting hydrocarbon chain containing 1-8 carbons is exemplified by methylene (—CH$_2$—), ethylene (—CH$_2$—CH$_2$—), propylene (—CH$_2$CH$_2$CH$_2$—), ethylidene [—CH—], 1,2-propylene
$\phantom{xxxxxxxxxxxxxxxxxxxxxxxxxxxxxxxxxxxxxx}|$
$\phantom{xxxxxxxxxxxxxxxxxxxxxxxxxxxxxxxxxxxxxx}$CH$_3$

[—CH—CH$_2$— or —CH$_2$—C—], isopropylidine [—C—], or
$\phantom{xx}|\phantom{xxxxxxxxxxxxxxxx}|\phantom{xxxxxxxxxxxxxxxxx}|$
$\phantom{xx}$CH$_3\phantom{xxxxxxxxxxxxxx}$CH$_3\phantom{xxxxxxxxxxxxxxxxx}$CH$_3$ 1,3-butylene [—CH—CH$_2$—CH$_2$—], and the like.
$\phantom{xxxxxxxxxxxx}|$
$\phantom{xxxxxxxxxxxx}$CH$_3$ The term "loweralkyl" includes straight and branched chain hydrocarbon radicals of up to eight carbon atoms inclusive and is exemplified by such groups as methyl, ethyl, propyl, isopropyl, butyl, isobutyl, tertiary butyl, amyl, isoamyl, hexyl, heptyl, octyl, and the like.

The term "halogen" includes chlorine, bromine, fluorine, and iodine, preferably chlorine, bromine and fluorine.

The term "4-substituted-1-piperazinyl" refers to piperazine substituted in the 4-position by loweralkyl or alkoxy-carbonyl blocking group which may subsequently be removed to give the unsubstituted piperazine.

Pharmaceutically acceptable acid addition salts are those salts formed by the pyridobenzodiazepines and the [2-[(aminopyridinyl)amino]phenyl]arylmethanones of Formula IIp hereinbelow of this invention with any acid which is physiologically compatible in warm blooded animals, such salts being formed either by strong or weak acids. Representative of strong acids are hydrochloric, sulfuric and phosphoric acids. Representative of weak acids are fumaric, maleic, succinic, oxalic, cyclohexamic and the like.

The 6-aryl-11H-pyrido[2,3-b][1,4]benzodiazepines and the 5,6-dihydro derivatives thereof encompassed by Formula I have the formula

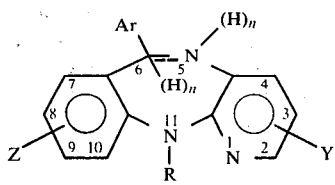

The 6-aryl-11H-pyrido[3,4-b][1,4]benzodiazepines and the 5,6-dihydro derivatives thereof encompassed by Formula I have the formula

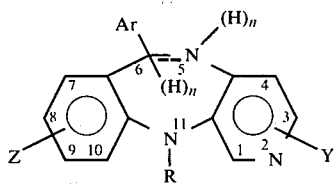

The 10-aryl-5H-pyrido[4,3-b][1,4]benzodiazepines and the 10,11 dihydro derivatives thereof encompassed by Formula I have the formula

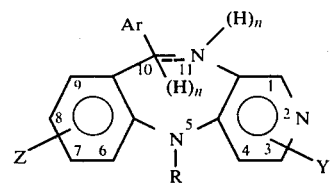

The 10-aryl-5H-pyrido[3,2-b][1,4]benzodiazepines and the 10,11 dihydro derivatives thereof encompassed by Formula I have the formula

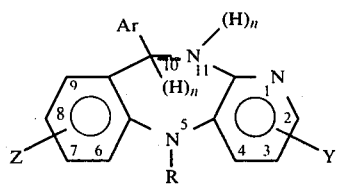

In all the formulas Iw to Iz, the symbols R, Ar, Z and Y have the definition given hereinabove under Formula I.

For the purpose of testing antidepressant activity of the present invention compounds, the procedure given by Englehardt, E. L., et al., J. Med. Chem. 11(2): 325 (1968) which has been indicative in the past of usefulness of compounds for treating human depression was used as follows: 20 mg/kg of the compound to be tested was administered to five adult female mice (ICR-DUB strain), intraperitoneally 30 minutes prior to the administration of a ptotic dose (32 mg/kg IP) of tetrabenazine (as the methane sulfonate salt). Thirty minutes later, the presence or absence of complete eyelid closure (ptosis) was assessed in each animal. An $ED_{50}$ (Median Effective Dose) may be established for each tested compound in blocking tetrabenazine induced ptosis in mice following the procedure given by Litchfield et al., J. Pharmacol. Exp. Therap. 96: 99–113 (1949).

Compounds of the invention encompassed by Formula I which have antidepressant activity in the foregoing procedure have the Formula Ip

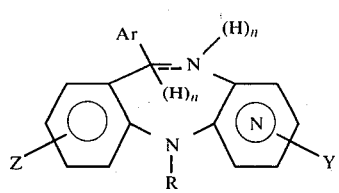

wherein;

R is selected from the group consisting of hydrogen, loweralkyl or -alk$^1$-N-R$^1$R$^2$;

R$^1$ and R$^2$ are selected from the group consisting of hydrogen, loweralkyl or R$^1$ and R$^2$ taken together with the adjacent nitrogen atom may form a heterocyclic residue selected from the group consisting of 1-pyrrolidinyl, 4-morpholinyl, 1-piperazinyl or 4-loweralkyl-1-piperazinyl;

Ar is selected from the group consisting of 2, 3 or 4-pyridinyl, 2 or 3-thienyl, phenyl or phenyl substituted by 1 to 3 radicals selected from halo, loweralkyl, loweralkoxy, trifluoromethyl or nitro and may be the same or different;

Alk$^1$ is a straight or branched hydrocarbon chain containing 1–8 carbon atoms;

Z is selected from the group consisting of hydrogen, halogen, loweralkyl, loweralkoxy, hydroxy or nitro;

Y is selected from the group consisting of hydrogen, or 1–2 radicals selected from loweralkyl, loweralkoxy or hydroxy and may be the same or different;

n is 0 and 1 and when n is zero the dotted line is a double bond, and the pharmaceutically acceptable acid addition salts thereof.

The compounds of Formula Ip wherein R is -alk$^1$-NR$^1$R$^2$ and and R$^1$ and R$^2$ are loweralkyl or hydrogen have been shown to have low incidence of antihistaminic, anticholinergic and cardiotoxic side effects when tested in animals.

The preferred pyridobenzodiazepines useful in the method of treating depression are as follows:

| Example No. | Compound active ingredient (free base) |
|---|---|
| 9 | N,N—dimethyl-6-phenyl-11H—pyrido[2,3-b][1,4]benzodiazepine-11-propanamine. |
| 23 | 6-(4-fluorophenyl)-N,N—dimethyl-11H—pyrido[2,3-b][1,4]benzodiazepine-11-propanamine. |
| 25 | 6-phenyl-11H—pyrido[2,3-b][1,4]benzodiazepine-11-propanamine. |
| 28 | N—methyl-6-phenyl-11H—pyrido[2,3-b][1,4]benzodiazepine-11-propanamine. |
| 52b | 6-(2-chlorophenyl)-N,N—dimethyl-11H—pyrido[2,3-b][1,4]benzodiazepine-11-propanamine. |
| 52a | 6-(2-fluorophenyl)-N,N—dimethyl-11H—pyrido[2,3-b][1,4]benzodiazepine-11-propanamine. |

Another compound within the scope of the present invention is 6-(2-fluorophenyl)-N-methyl-11H-pyrido[2,3-b][1,4]benzodiazepine-11-propanamine.

Compounds of the invention encompassed by Formula II which have antidepressant activity in the foregoing procedure have the Formula IIp

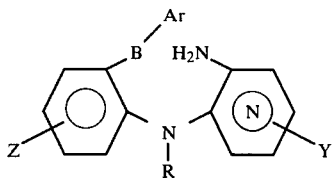

wherein;

R is selected from the group consisting of hydrogen, loweralkyl or —alk$^1$—NR$^1$R$^2$;

R$^1$ and R$^2$ are selected from the group consisting of hydrogen, loweralkyl, —C(O)—loweralkyl or R$^1$ and R$^2$ taken together with the adjacent nitrogen atom may form a heterocyclic residue selected from the group consisting of 1-piperidinyl, 1-phthalimido, 1-pyrrolidinyl, 4-morpholinyl, and 1-piperazinyl;

B is selected from carbonyl or thioxomethyl;

Ar, Z and Y are as defined under Formulas I and II above, and the pharmaceutically acceptable acid addition salts thereof.

The compounds of Formulas I and II wherein the R moiety carries a phthalimido, chloro, carbamoyl or imidate component are chemical intermediates rather than antidepressant agents, and compounds of Formula II wherein B is ketal or thioketal are also chemical intermediates rather than antidepressants.

It is therefore an object of the present invention to provide novel 6-aryl-11H-pyrido[1,4]benzodiazepines which have antidepressant activity.

Another object is to provide novel [2-[(aminopyridinyl)amino]phenyl]aryl methanones and their thioxomethyl, ketal or thioketal analogs.

Another object is to provide methods of treating depression and pharmaceutical compositions therefor.

Still another object is to provide novel intermediates for preparing aryl substituted-11H-pyrido[1,4]benzodiazepines which are antidepressants, certain of which intermediates also have antidepressant activity.

Additional objects and advantages of the present invention will be apparent to one skilled in the art and others will be apparent from the following description of the best mode of carrying out the present invention and from the appended claims.

DETAILED DESCRIPTION OF THE INVENTION

The present invention encompasses the novel pyridobenzodiazepines and methanone(thioxomethyl, ketal or thioketal analogs) intermediates as set forth herein in Formulas I and II as compositions of matter and utilization of these compounds as antidepressants or as intermediates in the preparation of other antidepressants.

Description of Compound Preparation.

Reaction sequence by equation for the preparation of the compounds of the invention is given in Chart 1. Alternate procedures for preparation of certain of the compounds are given by equation in Charts 2, 3, 4, 5 and 6.

Methanones, Formula II, See Chart 1.

The methanone (or analogs) intermediates are prepared by heating a mixture of the halo-amino pyridine and an aminobenzophenone (or analog) for a shorter period of time than that required for cyclization to the pyridobenzodiazepine as indicated by chemical ionization mass spec. analysis. For the [2-[(3-amino-2-pyridinyl)amino]phenyl]methanones, the conditions required are about 1 to 1.5 hr at 170°–200° C. The methanones and analogs may be isolated as the predominant product, if desired, by cooling and adding a suitable organic solvent such as, for example, methylene chloride which will dissolve unreacted starting materials and some cyclized compound (Ia) followed by usual methods of isolating such as partitioning between the solvent and aqueous base of methanolic aqueous base followed by washing, drying, evaporating the solvent layer and recrystallizing from a suitable solvent.

Unsubstituted Pyridobenzodiazepines, Formulas Ia and Ia-1 (R=H), See Chart 1.

The purified II compounds or crude II compounds may be further heated in an aprotic solvent to cyclize to compounds of Formula Ia, removing water from the reaction mixture by conventional means; for example, under refluxing using a Dean-Stark water trap. However, it is not necessary to stop heating at the intermediate stage; generally, it is sufficient to continue heating of the original reaction mixture, i.e., III+IV, for a longer period of time during which cyclization to Ia occurs. In the cyclization state, whichever alternative is used, the temperature time relationship will vary to some extent depending on the reactants used, it being only necessary to heat for a time sufficient to produce the product desired as indicated by chemical ionization mass spec. The unsubstituted pyridobenzodiazepines are purified by partitioning between a suitable solvent such as methylene chloride and aqueous base, washing and drying the solvent layer, evaporating and chromatographing in a suitable solvent system such as acetone-benzene. The corresponding dihydrodiazepine may be prepared by reduction with sodium borocyanohydrin.

Substituted Pyridobenzodiazepines. Formulas Ib and Ib-1 (R=loweralkyl), See Chart 1.

Preferably, compounds of Formula Ia (or Ia-1) wherein R is hydrogen are alkylated or alkylaminated or radicals are introduced which will lead to alkylamination by reacting first with sodium hydride and then with an appropriate reagent represented by halo-alk$^1$Q wherein "alk" has the meaning as defined above and Q is as defined in Chart 1. The compounds suspended in a suitable solent such as dimethyl formamide are added to a stirred suspension of sodium hydride in the same solvent. The halo-alk$^1$-Q reagent (alkylaminating agent or agent leading to alkylamination) is added at about room temperature and the reaction mixture is stirred for a period of time until reaction is complete as, for example, determined by thin layer chromatography. The unreacted sodium hydride is decomposed by adding to water and the product is extracted with a suitable solvent such as methylene chloride followed by aqueous acid extraction of the solvent layer and isolating the product from the aqueous layer by neutralization and re-extraction with methylene chloride followed by evaporation and precipitating, preferably as an addition salt such as fumarate, hydrochloride, oxalate, maleate and the like. Generally, once having obtained and purified an acid addition salt, the free base may be regenerated by partitioning the salt between an aqueous base and a suitable solvent such as methylene chloride and evaporating the methylene chloride layer. The corresponding dihydrodiazepines may be prepared by reduction with sodium borocyanohydrin. Alternately, compounds of Formulas Ib wherein Q is halo may be converted to compounds wherein Q is -N-(loweralkyl)$_2$ by reacting with an appropriate dialkylamine as given in the reaction sequence of Chart 2.

The primary amines of Formula Ic; i.e., $R^1$ and $R^2$ are both hydrogen, are prepared from the -alk$^1$-ω-(1-phthalimido) derivatives, as shown in Chart 1, by reacting with hydrazine hydrate, utilizing the method of Org. Syn. Coll. Vol. III, pp 151–153. Generally, about 2–3 hr reflux time is sufficient after which aqueous acid is added and the mixture is filtered. The primary -alk$^1$-amines are isolated from suitable solvents such as isopropyl alcohol. Hydrochlorides and hydrochloride hydrates are preferred salts in the isolation step. The corresponding dihydrodiazepines may be obtained by reduction with sodium borocyanohydrin.

The -alk$^1$-ω-monoalkylamines (Formula Ie); e.g., $R^1$=methyl, $R^2$=hydrogen, may be prepared as shown in Chart 1 by reacting the primary -alk$^1$-NH$_2$ derivatives Ic or Ic-1 with refluxing triethyl orthoformate for a period of time sufficient to form the methanimidic acid ester (I-d) which is then reacted with sodium borohydride. The unreacted borohydride is decomposed with water and the product extracted out with a suitable solvent such as ethyl acetate and may be purified by column chromatography and partitioning with basic solvent. Hydrochlorides are preferred salts in the isolation step. The method is more fully exemplified in Examples 27 and 28. The corresponding dihydrobenzodiazepines may then be prepared by reduction with sodium-borocyanohydrin.

-Alk$^1$-ω-monomethylamines may also be prepared by reaction of the primary amine with ethyl chloroformate as in Example 29, and thereafter reducing with lithium aluminum hydride as exemplified in Chart 3.

A further more generalized alternative for introduction of -alk$^1$-ω-monoloweralkyl amine radicals is via the radical:

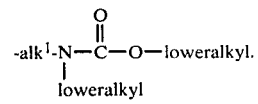

See Charts 1 and 4.

All formulas Ia, Ia-1, Ib, Ib-1, Ib-2, Ib-3, Ib-4, Ic, Ic-1, Ic-2, Id, Ie, and Ie-1 are encompassed by Formula I.

Compounds of Formula I wherein the -NR$^1$R$^2$ moiety is unsubstituted 1-piperazinyl are obtained by hydrolizing a compound of Formula I wherein —NR$^1$R$^2$ is piperazino substituted in the 4-position by an alkyl carbonyl such as t-butoxycarbonyl.

Compounds of Formula II wherein R is hydrogen may be alkylaminated by reacting with sodium hydride and an appropriate reagent represented by halo-alk$^1$-NR$^1$R$^2$ wherein "alk$^1$" has the meaning as defined above with the proviso that $R^1$ and $R^2$ are not hydrogen. See Chart 5 for the equation. The addition and subsequent removal of blocking agents on the NH$_2$ radical on the pyridine ring is anticipated as a means of improving yields. These compounds may then be cyclized to the pyrido[1,4]benzodiazepines.

Compounds of Formula II wherein B is carbonyl may also be prepared by hydrolyzing the appropriate pyrido[1,4]benzodiazepine with cold concentrated hydrochloric acid. See Chart 6 for the equation.

CHART 1

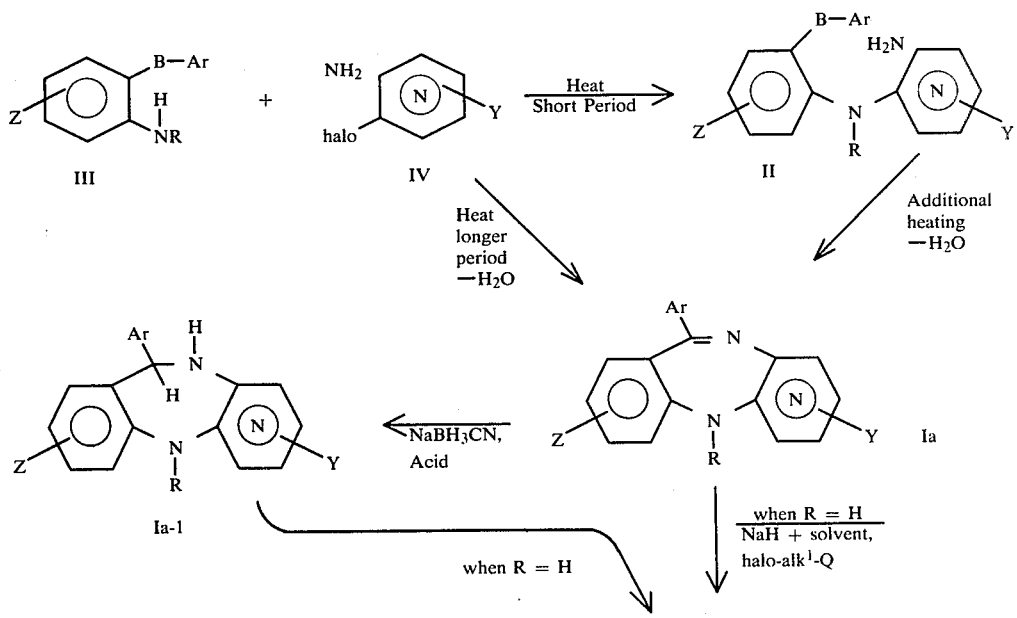

-continued
CHART 1
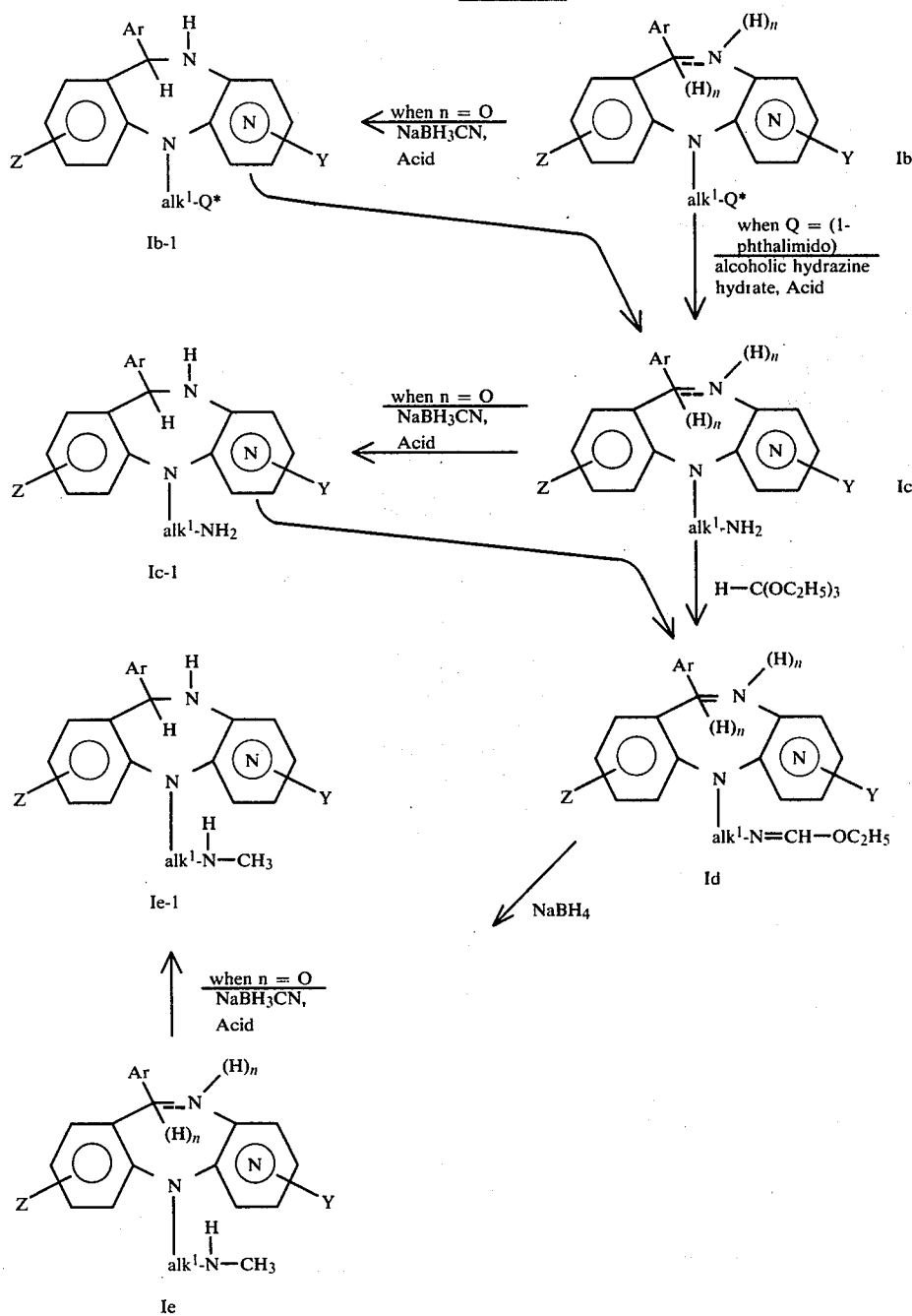
*Q is selected from the group consisting of hydrogen, —N—(loweralkyl)₂, 1-pyrrolidinyl, 1 piperidinyl, 4-substituted-1-piperazinyl, 4-morpholinyl, 1-phthalimido,
$$-N-\underset{\underset{loweralkyl}{|}}{\overset{\overset{O}{\|}}{C}}-O-loweralkyl, \text{ or halo.}$$
R = H, methyl or ethyl,
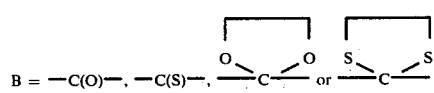

CHART 2

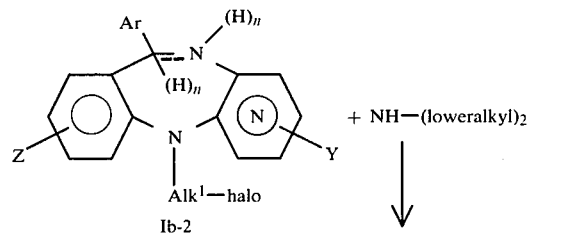

CHART 4

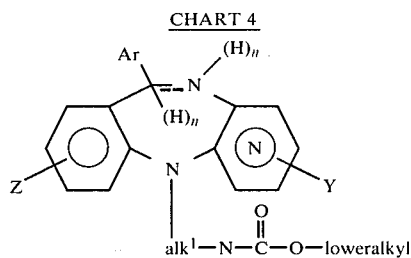

CHART 3

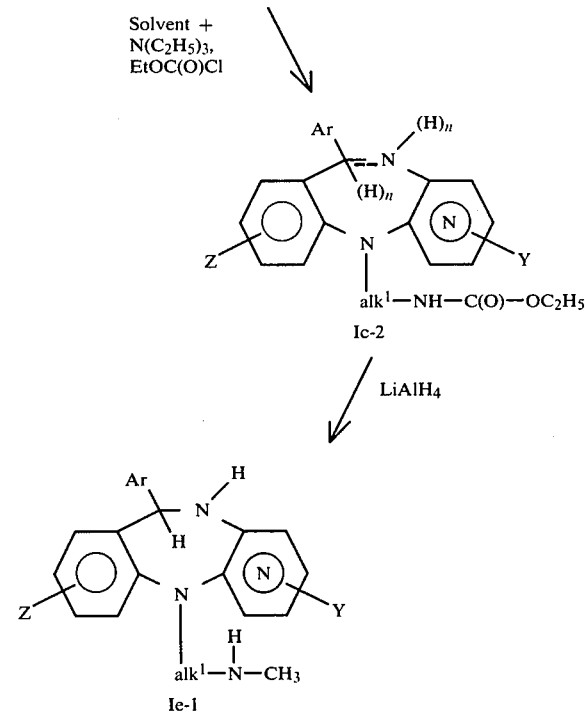

The preparation of the novel [(amino-pyridinyl)aminophenylaryl]methanones which are intermediates in the preparation of the aryl substituted-pyrido[1,4-]benzodiazepines are illustraed more fully in the following Intermediates 1 to 16. Structures of the intermediates are illustrated in Table 1.

CHART 5

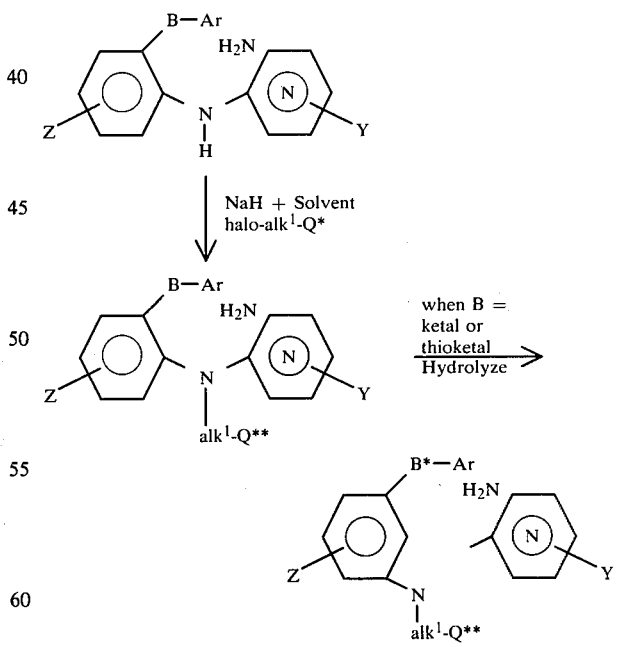

$Q^{**}$ is $-N-R^1R^2$ wherein $R^1$ and $R^2$ are as defined above.

B is $-C(O)-$, $-C(S)-$, [ketal O-C-O] or [thioketal S-C-S].
B* is $-C(O)-$ or $-C(S)-$.

CHART 6

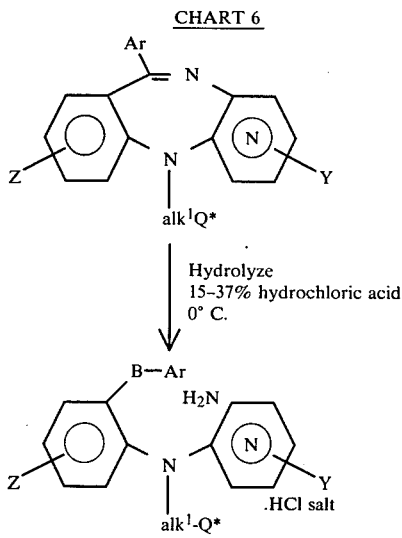

Q* is as defined in Chart 1.
B is —C(O)—.

Preparation of Methanone Intermediates

Intermediate 1

[2-[(3-Amino-2-pyridinyl)amino]phenyl]phenylmethanone

A stirred mixture of 39.4 g (0.20 mole) of 2-aminobenzophenone and 28.3 g (0.22 mole) of 3-amino-2-chloropyridine was heated at 180° C. under nitrogen atmosphere for 1.5 hr. The mixture was allowed to cool somewhat and 200 ml of methylene chloride was added slowly. After stirring for 3 hr and standing overnight at room temperature, 40.1 g of solid was filtered off and recrystallized twice from methanol:isopropyl ether giving 4.3 g, presumably the hydrochloride salt; m.p. 187°–90° C. This solid was dissolved in a mixture of water-methanol, basified with 3 N sodium hydroxide and extracted with methylene chloride. The combined methylene chloride extracts were dried over magnesium sulfate and evaporated under reduced pressure. The residue was recrystallized from isopropyl ether (charcoal) to give 2.1 g of product; m.p. 91°–3° C. Drying prior to analysis was overnight at room temperature/0.02 mm Hg.

Analysis: Calculated for $C_{18}H_{15}N_3O$: C,74.72; H,5.23; N,14.52. Found: C,74.94; H,5.23; N,14.69.

Intermediate 2

[2-[(3-Amino-2-pyridinyl)amino]-4-chlorophenyl]phenylmethanone

A stirred mixture of 23.2 g (0.1 mole) of 2-amino-4'-chlorobenzophenone and 14.2 g (0.11 mole) of 3-amino-2-chloropyridine was heated at 180° C. under nitrogen atmosphere for 2.5 hr. The mixture solidifed upon cooling to room temperature and was broken up with a spatula. The solid was suspended in 100 ml of methylene chloride and collected by filtration. The filter cake was dissolved in a mixture of water-methanol, basified with 3 N sodium hydroxide and extracted twice with methylene chloride. The combined methylene chloride extracts were dried over magnesium sulfate and evaporated under reduced pressure. The residue which had crystallized was triturated in isopropyl ether and the solid (16.7 g) collected by filtration. A 3 g sample was recrystallized from isopropyl ether to give 1.6 g product; m.p. 153°–155° C.

Analysis: Calculated for $C_{18}H_{14}ClN_3O$: C,66.77; H,4.36; N, 12.98. Found: C,67.06; H,4.36; N,13.17.

Intermediate 3

[2-[(3-Amino-2-(pyridinyl)amino]phenyl](4-methylphenyl)methanone

A stirred mixture of 20.0 g (0.095 mole) of 2-amino-4'-methylbenzophenone and 13.95 g (0.104 mole) of 3-amino-2-chloropyridine (96%) was heated under a nitrogen atmosphere at 180° C. for 2.0 hr. The mixture cooled to a glassy solid which was broken up, triturated in methylene chloride and the mixture stirred overnight. The solid was collected by filtration and dissolved in warm methanol. The solution was basified wiht 3 N sodium hydroxide, diluted with 500 ml of water and extracted 3 times with 250 ml of methylene chloride. The combined methylene chloride extracts were dried over magnesium sulfate and evaporated under reduced pressure. The residue which crystallized on standing was recrystallized twice from benzene-isooctane to give 4.2 g product, m.p. 126°–127.5° C.

Analysis: Calculated for $C_{19}H_{17}N_3O$: C,75.23; H,5.65; N,13.85. Found: C,75.81; H,5.69; N,13.96.

Intermediate 4

[2-[(3-Amino-2-pyridinyl)amino]-5-chlorophenyl]-(2-chlorophenyl)methanone

A stirred mixture of 20.0 g (0.156 mole) of 3-amino-2-chloropyridine and 37.3 g (0.14 mole) of 2-amino-2',5-dichlorobenzophenone was heated at 190° C. under nitrogen atmosphere for 5.5 hr. Thin layer chromatography (5% methyl alcohol-benzene on silica gel) indicated reaction had not substantially occurred. The mixture was stirred overnight at 190° C., cooled somewhat, and 100 ml methylene chloride was added cautiously. The suspension was stirred for two hr and the black solid which formed was separated by filtration. The solid was suspended in 500 ml of methylene chloride and 300 ml of dilute sodium hydroxide was added. An emulsion formed and the mixture was filtered which allowed separation of layers. The methylene chloride layer was washed with two 250 ml portions of water by extraction, dried over magnesium sulfate and evaporated under reduced pressure. The residue was dissolved in benzene and filtered through a 300 g column of florisil to remove low $R_f$ material. All fractions were combined and evaporated under reduced pressure. Thin layer chromatography showed presence of two major components with lower $R_f$ spot predominating. The residue was dissolved in benzene and chromatographed on a 600 g column of florisil packed in benzene. The higher $R_f$ material was eluted with 1% acetone-benzene. On evaporation, the residue was triturated in benzene and recrystallized from benzene-isooctane to give 2.7 g product; m.p. 162°–4° C.

Analysis: Calculated for $C_{18}H_{13}Cl_2N_3O$: C,60.35; H,3.66; N,11.73. Found: C,60.67; H,3.67; N,11.77.

Intermediates 5a to 5u

Following the procedures of Intermediate 3 and substituting equal molar amounts of the following for 2-amino-4'-methylbenzophenone:
2-amino-4'-ethylbenzophenone,
2-amino-4'-isopropylbenzophenone, 2-amino-4'-bromobenzophenone,
2-amino-3'-fluorobenzophenone,
2-amino-4'-ethoxybenzophenone,
2-amino-4'-nitrobenzophenone,
2-amino-4'-trifluoromethylbenzophenone,
2-amino-3'-methylbenzophenone,
2-amino-3'-ethylbenzophenone,
2-amino-3'-methoxybenzophenone,
2-amino-3'-ethoxybenzophenone,
2-amino-2'-nitrobenzophenone,
2-amino-3'-trifluoromethylbenzophenone,
2-amino-2'-methylbenzophenone,
2-amino-2'-ethylbenzophenone,
2-amino-2'-methoxybenzophenone,
2-amino-2',4'-dichlorobenzophenone,
2-amino-3',4',5'-trimethoxybenzophenone,
2-amino-2'-fluorobenzophenone,
2-amino-2'-chlorobenzophenone, and
2-amino-2'-bromobenzophenone,
there are obtained;
 (a) [2-[(3-amino-2-pyridinyl)amino]phenyl]-(4-ethylphenyl)methanone,
 (b) [2-[(3-amino-2-pyridinyl)amino]phenyl]-(4-isopropylphenyl)methanone,
 (c) [2-[(3-amino-2-pyridinyl)amino]phenyl]-(4-bromophenyl)methanone,
 (d) [2-[(3-amino-2-pyridinyl)amino]phenyl]-(3-fluorophenyl)methanone,
 (e) [2-[(3-amino-2-pyridinyl)amino]phenyl]-(4-ethoxyphenyl)methanone,
 (f) [2-[(3-amino-2-pyridinyl)amino]phenyl]-(4-nitrophenyl)methanone,
 (g) [2-[(3-amino-2-pyridinyl)amino]phenyl]-(4-trifluoromethylphenyl)methanone,
 (h) [2-[(3-amino-2-pyridinyl)amino]phenyl]-(3-methylphenyl)methanone,
 (i) [2-[(3-amino-2-pyridinyl)amino]phenyl]-(3-ethylphenyl)methanone,
 (j) [2-[(3-amino-2-pyridinyl)amino]phenyl]-(3-methoxyphenyl)methanone,
 (k) [2-[(3-amino-2-pyridinyl)amino]phenyl]-(3-ethoxyphenyl)methanone,
 (l) [2-[(3-amino-2-pyridinyl)amino]phenyl]-(2-nitrophenyl)methanone,
 (m) [2-[(3-amino-2-pyridinyl)amino]phenyl]-(3-trifluoromethylphenyl)methanone,
 (n) [2-[(3-amino-2-pyridinyl)amino]phenyl]-(2-methylphenyl)methanone,
 (o) [2-[(3-amino-2-pyridinyl)amino]phenyl]-(2-ethylphenyl)methanone,
 (p) [2-[(3-amino-2-pyridinyl)amino]phenyl]-(2-methoxyphenyl)methanone,
 (q) [2-[(3-amino-2-pyridinyl)amino]phenyl]-(2,4-dichlorophenyl)methanone,
 (r) [2-[(3-amino-2-pyridinyl)amino]phenyl]-(3,4,5-trimethoxyphenyl)methanone,
 (s) [2-[(3-amino-2-pyridinyl)amino]phenyl]-(2-fluorophenyl)methanone,
 (t) [2-[(3-amino-2-pyridinyl)amino]phenyl]-(2-chlorophenyl)methanone, and
 (u) [2-[(3-amino-2-pyridinyl)amino]phenyl]-(2-bromophenyl)methanone.

Intermediates 6a to 6o

Following the procedure of Intermediate 2 and substituting equal molar amounts of the following for 2-amino-4-chlorobenzophenone:
2-amino-5-chlorobenzophenone,
2-amino-6-chlorobenzophenone,
2-amino-4-fluorobenzophenone,
2-amino-4-bromobenzophenone,
2-amino-4-trifluoromethylbenzophenone,
2-amino-4-methylbenzophenone,
2-amino-5-methylbenzophenone,
2-amino-6-methylbenzophenone,
2-amino-4-ethylbenzophenone,
2-amino-4-methoxybenzophenone,
2-amino-4-ethoxybenzophenone,
2-amino-4-nitrobenzophenone,
2-amino-5-nitrobenzophenone,
2-amino-3-methylbenzophenone, and
2-amino-3-chlorobenzophenone,
there are obtained:
 (a) [2-[(3-amino-2-pyridinyl)amino]-5-chlorophenyl]phenylmethanone,
 (b) [2-[(3-amino-2-pyridinyl)amino]-6-chlorophenyl]phenylmethanone,
 (c) [2-[(3-amino-2-pyridinyl)amino]-4-fluorophenyl]phenylmethanone,
 (d) [2-[(3-amino-2-pyridinyl)amino]-4-bromophenyl]phenylmethanone,
 (e) [2-[(3-amino-2-pyridinyl)amino]-4-trifluoromethylphenyl)phenylmethanone,
 (f) [2-[(3-amino-2-pyridinyl)amino]-4-methylphenyl]phenylmethanone,
 (g) [2-[(3-amino-2-pyridinyl)amino]-5-methylphenyl]phenylmethanone,
 (h) [2-[(3-amino-2-pyridinyl)amino]-6-methylphenyl]phenylmethanone,
 (i) [2-[(3-amino-2-pyridinyl)amino]-4-ethylphenyl]phenylmethanone,
 (j) [2-[(3-amino-2-pyridinyl)amino]-4-methoxyphenyl]phenylmethanone,
 (k) [2-[(3-amino-2-pyridinyl)amino]-4-ethoxyphenyl]phenylmethanone,
 (l) [2-[(3-amino-2-pyridinyl)amino]-4-nitrophenyl]phenylmethanone,
 (m) [2-[(3-amino-2-pyridinyl)amino]-5-nitrophenyl]phenylmethanone,
 (n) [2-[(3-amino-2-pyridinyl)amino]-3-methylphenyl]phenylmethanone, and
 (o) [2-[(3-amino-2-pyridinyl)amino]-3-chlorophenyl]phenylmethanone.

Intermediates 7a to 7c

Following the procedure of Intermediate 1 and substituting equal molar amounts of the following for 3-amino-2-chloropyridine:
4-amino-3-chloropyridine,
3-amino-4-chloropyridine, and
2-amino-3-chloropyridine,
there are obtained:
 (a) [2-[(4-amino-3-pyridinyl)amino]phenyl]phenylmethanone,
 (b) [2-[(3-amino-4-pyridinyl)amino]phenyl]phenylmethanone, and
 (c) [2-[(2-amino-3-pyridinyl)amino]phenyl]phenylmethanone.

Intermediate 8

[2-[(3-Amino-2-pyridinyl)amino]phenyl](3-chlorophenyl)methanone

A stirred mixture of 35 g (0.152 mole) of 2-amino-3'-chlorobenzophenone and 23.4 g (0.182 mole) of 3-amino-2-chloropyridine was heated at 180° C. for 2 hr.

The hot melt was allowed to cool to 110° C., after which 100 ml of hot toluene was added dropwise with vigorous stirring. The mixture was allowed to cool while stirring to 30° C. and 50 ml of methylene chloride was added. After stirring for an additional ½ hour, the mixture was filtered and the filter cake suspended in methylene chloride with stirring for ½ hr and methylene chloride was separated by filtration. The filter cake containing the product (25.4 g) was partially dissolved in hot methanol (total volume 150 ml) and 50% aqueous sodium hydroxide was added until the mixture was basic. Ice water was added and the solution was extracted with methylene chloride. This methylene chloride extract was washed with water and dried over magnesium sulfate and evaporated to dryness. The residue was dissolved in isopropyl alcohol and boiled with charcoal. The mixture was filtered, reduced in volume to give a first crop of crystals weighing 16 g (33%). A portion of the crystals was recrystallized from isopropyl alcohol to give a brick red solid melting 119°-120° C.

Analysis: Calculated for: C,66.77; H,4.36; N,12.98. Found: C,66.78; H,4.42; N,12.94.

Intermediate 9

[2-[(3-Amino-2-pyridinyl)amino]phenyl](4-fluorophenyl)methanone

A stirred mixture of 35 g (0.163 mole) of 2-amino-4'-fluorobenzophenone and 27 g (0.21 mole) of 3-amino-2-chloropyridine was heated at 175°-180° C. for 2.5 hr. The mixture was allowed to cool to 110° C., after which 100 ml of hot toluene was added. On cooling to 50° C., 50 ml of methylene chloride was added. The solvent layer was decanted, leaving a black solid mass which was dissolved in hot methanol. The solution volume was reduced by one half and allowed to stand overnight at room temperature. The mixture was filtered and the filter cake washed twice by suspending in methylene chloride. The weight of crude solid produced was 22.5 g. The solid was dissolved in methanol and basified with 50% aqueous sodium hydroxide. The mixture was extracted with methylene chloride and the extract dried and concentrated. The residue was twice crystallized from isopropyl alcohol, decolorizing by boiling with charcoal the second time, to give 14 g (28%) solid which was red-orange in color; m.p. 121.5°-122.5° C.

Analysis: Calculated for $C_{18}H_{14}N_3OF$: C,70.35; H,4.59; N,13.67. Found: C,70.23; H,4.59 N,13.64.

Intermediate 10

[2-[(3-Amino-2-pyridinyl)amino]phenyl](2-thienyl)methanone

In accordance with the procedure of Intermediate 9, (2-aminophenyl)(2-thienyl)methanone, prepared by the method of Steinkopf & Gunther, Ann. 522, 28-34 (1936), is reacted with 3-amino-2-chloropyridine to give the title compound.

Intermediate 11

[2-[(3-Amino-2-pyridinyl)amino]phenyl](3-thienyl)methanone

In accordance with the procedure of Intermediate 9, (2-aminophenyl)(3-thienyl)methanone is reacted with 3-amino-2-chloropyridine to give the title compound.

Intermediate 12

[2-[(3-Amino-2-pyridinyl)amino]phenyl](2-pyridinyl)methanone

The title compound is prepared by reacting (2-aminophenyl)(2-pyridinyl)methanone, as prepared by Schofield, K., J. Chem. Soc. 1949, 2408-12, with 3-amino-2-chloropyridine.

Intermediate 13

[2-[(3-Amino-2-pyridinyl)amino]phenyl](3-pyridinyl)methanone

The title compound is prepared by reacting (2-aminophenyl)(3-pyridinyl)methanone as prepared by Abramovitch R. A. & Tertzakian, G., Tetrahedron Letters, 1963, 1511-15 and Abramovitch, R. A. et al., Can. J. Chem. 43(4), 725-31 (1965) with 3-amino-2-chloropyridine.

Intermediate 14

[2-[(3-Amino-2-pyridinyl)amino]phenyl](4-pyridinyl)methanone

The title compound is prepared by reacting (2-aminophenyl)(4-pyridinyl)methanone as prepared by Nann, A. J. and Schofield, K., J. Chem. Soc. 1952, 583-9 with 3-amino-2-chloropyridine.

Intermediates 15a to 15g

Following the procedure of Intermediate 1 and substituting equal molar amounts of the following for 3-amino-2-chloropyridine:
3-amino-2-chloro-4-methylpyridine,
3-amino-2-chloro-5-methylpyridine,
3-amino-2-chloro-6-methylpyridine,
3-amino-2-chloro-5,6-dimethylpyridine,
3-amino-2-chloro-6-methoxypyridine,
3-amino-4-chloro-2-methylpyridine, and
3-amino-2-chloro-5-methylpyridine,
there are obtained:
(a) [2-[(3-amino-4-methyl-2-pyridinyl)amino]phenyl]-phenylmethanone,
(b) [2-[(3-amino-5-methyl-2-pyridinyl)amino]phenyl]-phenylmethanone,
(c) [2-[(3-amino-6-methyl-2-pyridinyl)amino]phenyl]-phenylmethanone,
(d) [2-[(3-amino-5,6-dimethyl-2-pyridinyl)amino]-phenyl]phenylmethanone,
(e) [2-[(3-amino-6-methoxy-2-pyridinyl)amino]-phenyl]phenylmethanone,
(f) [2-[(3-amino-2-methyl-4-pyridinyl)amino]phenyl]-phenylmethanone, and
(g) [2-[(3-amino-5-methoxy-2-pyridinyl)amino]-phenyl]phenylmethanone.

Intermediates 16a to 16f

Following the procedure of Intermediate 1 and substituting equal molar amounts of the following for 3-amino-2-chloropyridine:
2-amino-3-chloro-5-methylpyridine,
2-amino-3-chloro-4,6-dimethylpyridine,
2-amino-3-chloro-5-ethylpyridine,
4-amino-3-chloro-5-methylpyridine,
4-amino-3-chloro-2,6-dimethylpyridine, and
4-amino-3-chloro-2-methylpyridine,
there are obtained:

(a) [2-[(2-amino-5-methyl-3-pyridinyl)amino]phenyl]-phenylmethanone,
(b) [2-[(2-amino-4,6-dimethyl-3-pyridinyl)amino]-phenyl]phenylmethanone,
(c) [2-[(2-amino-5-ethyl-3-pyridinyl)amino]phenyl]-phenylmethanone,
(d) [2-[(4-amino-5-methyl-3-pyridinyl)amino]phenyl]-phenylmethanone,
(e) [2-[(4-amino-6-methyl-3-pyridinyl)amino]phenyl]-phenylmethanone, and
(f) [2-[(4-amino-2-methyl-3-pyridinyl)amino]phenyl]-phenylmethanone.

Intermediate 17a-c

Following the procedure of Intermediate 1 and substituting equal molar amounts of the following for 2-aminobenzophenone and adding an inorganic base to neutralize the acid formed:
(2-aminophenyl)phenylmethanethione,
2-(2-phenyl-1,3-dioxolan-2-yl)benzeneamine, and
2-(2-phenyl-1,3-dithiolan-2-yl)benzeneamine,
there are obtained
(a) [2-[(3-amino-2-pyridinyl)amino]phenyl]phenylmethanethione,
(b) $N^2$-[2-(2-phenyl-1,3-dioxolan-2-yl)phenyl]-2,3-pyridinediamine, and
(c) $N^2$-[2-(2-phenyl-1,3-dithiolan-2-yl)phenyl]-2,3-pyridinediamine.

Intermediate 18

[2-[(3-Amino-2-pyridinyl)-N-methylamino]phenyl]-phenylmethanone hydrochloride

Following the procedure of Intermediate 1, 2-N-methyl aminobenzophenone is reacted with 3-amino-2-chloropyridine to give the title compound. The free base of the title compound is obtained also by the latter part of the procedure of Intermediate 1.

Intermediate 19

[2-[(3-Amino-2-pyridinyl)-N-ethylamino]phenyl]-phenylmethanone hydrochloride

Following the procedure of Intermediate 1, 2-N-ethylaminobenzophenone is reacted with 3-amino-2-chloropyridine to give the title compound. The free base of the title compound is obtained also by the latter part of the procedure of Intermediate 1.

Intermediate 20

[2-[(3-Amino-2-pyridinyl)[3-(dimethylamino)propyl]amino]phenyl]phenylmethanone

A solution of N,N-dimethyl-6-phenyl-11H-pyrido[2,3-b][1,4]benzodiazepine-11-propanamine in isopropyl alcohol is treated with 25% hydrochloric acid at 0° C. to give a solution of the title compound.

Intermediate 21

[2-[[3-(Dimethylamino)propyl](3-amino-2-pyridinyl)amino]phenyl]phenylmethanone

To a stirred suspension of sodium hydride (in mineral oil) in anhydrous dimethylformamide, under nitrogen atmosphere was added, portionwise, [2-[(3-amino-2-pyridinyl)amino]phenyl]phenylmethanone. To the mixture was added 3-dimethylaminopropyl chloride hydrochloride to give a solution containing some of the title compound as indicated by chemical ionization mass spectrascopy analysis. With time, this cyclized spontaneously to the corresponding pyrido[2,3-b][1,4]benzodiazepine.

Intermediate 22

[2-[(3-Amino-2-pyridinyl)[3-(dimethylamino)propyl]amino]phenyl]phenylmethione

To a stirred suspension of sodium hydride (in mineral oil) in anhydrous dimethylformamide under nitrogen atmosphere is added, portionwise, [2-[(3-amino-2-pyridinyl)amino]phenyl]phenylmethanethione. To the mixture is added 3-dimethylaminopropyl chloride hydrochloride to give a solution containing the title compound.

Intermediate 23

$N^2$-[3-(Dimethylamino)propyl]-$N^2$-[2-(2-phenyl-1,3-dioxolan-2-yl)phenyl]-2,3-pyridinediamine To a stirred suspension of sodium hydride (in mineral oil) in anhydrous dimethylformamide under nitrogen atmosphere is added, portionwise, $N^2$-[2-(2-phenyl-1,3-dioxolan-2-yl)phenyl]-2,3-pyridinediamine. To the mixture is added 3-dimethylaminopropyl chloride hydrochloride to give a solution containing the title compound.

Intermediate 24

$N^2$-[3-(Dimethylamino)propyl]-$N^2$-[2-(2-phenyl-1,3-dithiolan-2-yl)phenyl]-2,3-pyridinediamine To a stirred suspension of sodium hydride (in mineral oil) in anhydrous dimethylformamide under nitrogen atmosphere is added, portionwise, $N^2$-[2-(2-phenyl-1,3-dithiolan-2-yl)phenyl]-2,3-pyridinediamine. To the mixture is added 3-dimethylaminopropyl chloride hydrochloride to give a solution containing the title compound.

TABLE 1

| Intermediate | Ar | B | Y | R | Z |
|---|---|---|---|---|---|
| 1 | $C_6H_5$— | —C(O)— | H | H | H |
| 2 | $C_6H_5$— | —C(O)— | H | H | 4-Cl |
| 3 | 4-$CH_3$—$C_6H_4$— | —C(O)— | H | H | H |
| 4 | 2-Cl—$C_6H_4$— | —C(O)— | H | H | 5-Cl |
| 5a | 4-$C_2H_5$—$C_6H_4$— | —C(O)— | H | H | H |

TABLE 1-continued

| Intermediate | Ar | B | Y | R | Z |
|---|---|---|---|---|---|
| 5b | 4-i-$C_3H_7$—$C_6H_4$— | —C(O)— | H | H | H |
| 5c | 4-Br—$C_6H_4$— | —C(O)— | H | H | H |
| 5d | 3-F—$C_6H_4$— | —C(O)— | H | H | H |
| 5e | 4-$OC_2H_5$—$C_6H_4$— | —C(O)— | H | H | H |
| 5f | 4-$NO_2$—$C_6H_4$— | —C(O)— | H | H | H |
| 5g | 4-$CF_3$—$C_6H_4$— | —C(O)— | H | H | H |
| 5h | 3-$CH_3$—$C_6H_4$— | —C(O)— | H | H | H |
| 5i | 3-$C_2H_5$—$C_6H_4$— | —C(O)— | H | H | H |
| 5j | 3-$OCH_3$—$C_6H_4$— | —C(O)— | H | H | H |
| 5k | 3-$OC_2H_5$—$C_6H_4$— | —C(O)— | H | H | H |
| 5l | 2-$NO_2$—$C_6H_4$— | —C(O)— | H | H | H |
| 5m | 3-$CF_3$—$C_6H_4$— | —C(O)— | H | H | H |
| 5n | 2-$CH_3$—$C_6H_4$— | —C(O)— | H | H | H |
| 5o | 2-$C_2H_5$—$C_6H_4$— | —C(O)— | H | H | H |
| 5p | 2-$OCH_3$—$C_6H_4$— | —C(O)— | H | H | H |
| 5q | 2,4-$Cl_2$—$C_6H_3$— | —C(O)— | H | H | H |
| 5r | 3,4,5-$(OCH_3)_3$—$C_6H_2$— | —C(O)— | H | H | H |
| 5s | 2-F—$C_6H_4$— | —C(O)— | H | H | H |
| 5t | 2-Cl—$C_6H_4$ | —C(O)— | H | H | H |
| 5u | 2-Br—$C_6H_4$ | —C(O)— | H | H | H |
| 6a | $C_6H_5$— | —C(O)— | H | H | 5-Cl |
| 6b | $C_6H_5$— | —C(O)— | H | H | 6-Cl |
| 6c | $C_6H_5$— | —C(O)— | H | H | 4-F |
| 6d | $C_6H_5$— | —C(O)— | H | H | 4-Br |
| 6e | $C_6H_5$— | —C(O)— | H | H | 4-$CF_3$ |
| 6f | $C_6H_5$— | —C(O)— | H | H | 4-Me |
| 6g | $C_6H_5$— | —C(O)— | H | H | 5-Me |
| 6h | $C_6H_5$— | —C(O)— | H | H | 6-$CH_3$ |
| 6i | $C_6H_5$— | —C(O)— | H | H | 4-$C_2H_5$ |
| 6j | $C_6H_5$— | —C(O)— | H | H | 4-$OCH_3$ |
| 6k | $C_6H_5$— | —C(O)— | H | H | 4-$OC_2H_5$ |
| 6l | $C_6H_5$— | —C(O)— | H | H | 4-$NO_2$ |
| 6m | $C_6H_5$— | —C(O)— | H | H | 5-$NO_2$ |
| 6n | $C_6H_5$— | —C(O)— | H | H | 3-$CH_3$ |
| 6o | $C_6H_5$— | —C(O)— | H | H | 3-Cl |
| 8 | 3-Cl—$C_6H_4$— | —C(O)— | H | H | H |
| 9 | 4-F—$C_6H_4$— | —C(O)— | H | H | H |
| 10 | 2-thienyl | —C(O)— | H | H | H |
| 11 | 3-thienyl | —C(O)— | H | H | H |
| 12 | 2-pyridinyl | —C(O)— | H | H | H |
| 13 | 3-pyridinyl | —C(O)— | H | H | H |
| 14 | 4-pyridinyl | —C(O)— | H | H | H |
| 15a | $C_6H_5$— | —C(O)— | 4-$CH_3$ | H | H |
| 15b | $C_6H_5$— | —C(O)— | 5-$CH_3$ | H | H |
| 15c | $C_6H_5$— | —C(O)— | 6-$CH_3$— | H | H |
| 15d | $C_6H_5$— | —C(O)— | 5,6-$(CH_3)_2$ | H | H |
| 15e | $C_6H_5$— | —C(O)— | 6-$OCH_3$ | H | H |
| 15g | $C_6H_5$— | —C(O)— | 5-$OCH_3$ | H | H |
| 17a | $C_6H_5$— | —C(S)— | H | H | H |
| 17b | $C_6H_5$— | 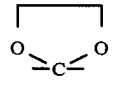 | H | H | H |
| 17c | $C_6H_5$— | 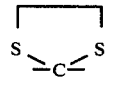 | H | H | H |
| 18 | $C_6H_5$— | —C(O)— | H | —$CH_3$ | H |
| 19 | $C_6H_5$— | —C(O)— | H | —$C_2H_5$ | H |
| 20 | $C_6H_5$— | —C(O)— | H | —$(CH_2)_3$N—$(CH_3)_2$ | H |
| 21 | $C_6H_5$— | —C(O)— | H | —$(CH_2)_3$N$(CH_3)_2$ | H |
| 22 | $C_6H_5$— | —C(S)— | H | —$(CH_2)_3$N—$(CH_3)_2$ | H |
| 23 | $C_6H_5$ | 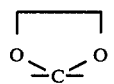 | H | —$(CH_2)_3$N—$(CH_3)_2$ | H |
| 24 | $C_6H_5$— | 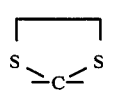 | H | —$(CH_2)_3$N—$(CH_3)_2$ | H |

TABLE 1-continued

| Intermediate | Ar | B | Y | R | Z |
|---|---|---|---|---|---|
| 7a | C$_6$H$_5$— | —C(O)— | H | H | H |
| 16d | C$_6$H$_5$— | —C(O)— | 5-CH$_3$ | H | H |
| 16e | C$_6$H$_5$— | —C(O)— | 6-CH$_3$ | H | H |
| 16f | C$_6$H$_5$— | —C(O)— | 2-CH$_3$ | H | H |
| 7b | C$_6$H$_5$— | —C(O)— | H | H | H |
| 15f | C$_6$H$_5$— | —C(O)— | 2-CH$_3$ | H | H |
| 7c | C$_6$H$_5$— | —C(O)— | H | H | H |
| 16a | C$_6$H$_5$— | —C(O)— | 5-CH$_3$ | H | H |
| 16b | C$_6$H$_5$— | —C(O)— | 4,6(CH$_3$)$_2$ | H | H |
| 16c | C$_6$H$_5$— | —C(O)— | 5-C$_2$H$_5$ | H | H |

The preparation of novel phenyl-substituted pyrido[1,4]-benzodiazepine compounds of the present invention and the novel process is exemplified more fully by the following examples. Structures of the compounds of the examples are illustrated in Table 2. The scope of the invention is not limited thereto, however.

EXAMPLE 1

6-Phenyl-11H-pyrido[2,3-b][1,4]benzodiazepine

A mixture of 19.7 g (0.1 mole) of 2-aminobenzophenone and 15.0 g (0.12 mole) of 3-amino-2-chloropyridine was heated under nitrogen atmosphere at 190° C. for 1.75 hr. The mixture was cooled to room temperature and partitioned between 3 N aqueous sodium hydroxide and methylene chloride. The combined methylene chloride extracts were washed with water, dried over magnesium sulfate and evaporated under reduced pressure. The residue, 32.7 g, was dissolved in benzene and chromatographed on a column of florisil packed in benzene, eluting with benzene and 1–2% acetone-benzene mixtures. After evaporation, the solid was crystallized from benzene to give 7.3 g product; m.p. 106°–108° C.

Analysis: Calculated for C$_{18}$H$_{13}$N$_3$: C,79.68; H,4.83; N,15.49. Found: C,79.70; H,4.81; N,15.42.

EXAMPLE 2

8-Chloro-6-phenyl-11H-pyrido[2,3-b][1,4]benzodiazepine

A mixture of 15.0 g (0.0647 mole) of 2-amino-5-chlorobenzophenone and 9.1 g (0.068 mole) of 3-amino-2-chloropyridine was heated at 200° C. (in an oil bath) for 0.75 hr under nitrogen atmosphere. The mixture was cooled and methylene chloride added. The mixture was stirred for 1 hr then allowed to stand overnight. Brown solid precipitate weighing 8.7 g was separated by filtration. The filtrate was evaporated under reduced pressure. The residue was combined with the brown solid and partitioned with aqueous sodium hydroxide and methylene chloride and crude product isolated as in Example 1, except the crystallizing solvent was ethanol. Recrystallization from ethanol and drying over night at 82° C./0.1 mm Hg gave 3.0 g product; m.p. 156.5°–158.5° C.

Analysis: Calculated for C$_{18}$H$_{12}$ClN$_3$: C,70.71; H,3.96; N,13.74. Found: C,70.24; H,4.01; N,13.76.

EXAMPLE 3

9-Chloro-6-phenyl-11H-pyrido[2,3-b][1,4]benzodiazepine

A suspension of 6.6 g (0.02 mole) of [2-[(3-amino-2-pyridyl)amino]-4-chlorophenyl]-(phenyl)methanone (Intermediate 2) in 200 ml of toluene was heated at reflux over night under nitrogen atmosphere. The reaction mixture was filtered hot and the filtrate heated back to reflux temperature. The precipitate formed in cooling to room temperature was separated by filtration and recrystallized from benzene and dried 4 hr at 97°–98° C./0.1 mm Hg and over night at room temperature/0.1 mm Hg to give 3.7 g; m.p. 250.5° to 252° C. Elemental analysis for carbon was high and the product was redried at 139° C. (xylenes in drying pistol) for 8 hr. Although the carbon analysis remained high, the proton nuclear magnetic resonance spectrum and mass spectrum was consistent with the proposed structure.

Analysis: Calculated for $C_{16}H_{12}ClN_3$: C,70.71; H,3.96; N,13.74. Found: C,71.46; H,4.06; N,13.46.

EXAMPLE 4

8-Chloro-6-(2-chlorophenyl)-5,6-dihydro-11H-pyrido[2,3-b][1,4]benzodiazepine

Further elution of the florisil column in the preparation of Intermediate 4 with 10–15% acetone in benzene and 5–25% methanol in benzene gave two fractions of the title product of this example, 6.4 g and 5.7 g, the second being quite impure. The 6.4 g fraction was recrystallized from benzeneisooctane to give 3.7 g of solid; m.p. 203°–6° C. (decomposition) which was identified by chemical ionization mass spec. analysis, $^1H$ and $^{13}C$ NMR as 8-chloro-6-(2-chlorophenyl)-5,6-dihydro-11H-pyrido[2,3-b][1,4]benzodiazepine.

EXAMPLE 5

6-(4-Chlorophenyl)-11H-pyrido[2,3-b][1,4]benzodiazepine

A mixture of 23.2 g (0.10 mole) of 2-amino-4'-chlorobenzophenone and 14.7 g (0.11 mole) of 3-amino-2-chloropyridine (96%) were heated for 1.5 hr at 180° C. under nitrogen atmosphere. The mixture was cooled to room temperature and methylene chloride added. After stirring for 30 min., solids were separated by filtration and triturated in hot 190 proof ethanol. The remaining insoluble material was collected by filtration and recrystallized from benzeneisooctane to give 2.7 g product, m.p. 203°–204.5° C. Drying conditions prior to analyses were: overnight at 97°–98° C./0.1 mm Hg.

Analysis: Calculated for $C_{18}H_{12}ClN_3$: C,70.71; H,3.96; N,13.74 Found: C,70.76; H,3.92; N,13.95

EXAMPLE 6

6-(4-Methylphenyl)-11H-pyrido[2,3-b][1,4]benzodiazepine

A solution of 3.6 g (0.012 mole) of [2-[(3-amino-2-pyridyl)amino]phenyl](4-methylphenyl)methanone in 100 ml of anhydrous toluene was treated with a catalytic amount of para toluene sulfonic acid and refluxed overnight while separating water with a Dean-Stark trap. The reaction mixture was filtered while hot. The product precipitated as the filtrate cooled to room temperature and was collected by filtration. Weight of solid after solvent evaporated was 2.5 g, m.p. 203.5°–205° C. (decomp.).

Analysis: Calculated for $C_{19}H_{15}N_3$: C,79.98; H,5.30; N,14.73. Found: C,79.95; H,5.27; N,14.96.

EXAMPLE 7

6-(4-Methoxyphenyl)-11H-pyrido[2,3-b][1,4]benzodiazepine

A stirred mixture of 20.0 g (0.088 mole) of 2-amino-4'-methoxybenzophenone and 13.0 g (0.097 mole) of 3-amino-2-chloropyridine (96%) was heated at 180° C. under a nitrogen atmosphere for 2.0 hr. The reaction mixture was cooled to approximately 70° C. and 100 ml of methylene chloride was added slowly. After the mixture had cooled to room temperature, another 50 ml of methylene chloride was added and the mixture was stirred overnight. The suspended solid was collected by filtration, air dried, dissolved in methanol and basified with 3 N sodium hydroxide. The suspension was diluted with 500 ml water and extracted with three 250 ml portions of methylene chloride. The combined methylene chloride extracts were dried over magnesium sulfate and evaporated under reduced pressure. Analysis by mass spectra (EI and CI) indicated the residue was a mixture of [2-[(3-amino-2-pyridyl)amino]phenyl](4-methoxyphenyl)methanone and the title compound. The residue-mixture was dissolved in 250 ml toluene with a catalytic amount of para toluene sulfonic acid and the solution was refluxed overnight under a nitrogen atmosphere while separating water in a Dean-Stark trap. The reaction mixture was filtered while hot. The product precipitated as the filtrate cooled to room temperature and was collected by filtration. After recrystallization from benzene the product weighed 1.8 g, m.p. 198.5°–200°–5° C. (d).

Analysis: Calculated for $C_{19}H_{15}N_3O$: C,75.73; H,5.02; N,13.94. Found: C,75.65; H,4.98; N,14.03.

EXAMPLE 8

8-Chloro-N,N-dimethyl-6-phenyl-11H-pyrido[2,3-b][1,4]benzodiazepine-11-propanamine oxalate [1:1]

To a stirred suspension of 1.05 g (0.044 mole) of sodium hydride (in mineral oil) in 50 ml of anhydrous dimethylformamide, under nitrogen atmosphere was added, portionwise, 6.1 g (0.02 mole) of 8-chloro-6-phenyl-11H-pyrido[2,3-b][1,4]benzodiazepine. The reaction mixture was stirred at room temperature for 1.5 hr, during which evolution of hydrogen ceased. To the mixture was added, portionwise, 3.5 g (0.022 mole) of 3-dimethylaminopropylchloride hydrochloride. After stirring overnight at room temperature, the reaction mixture was poured into 1600 ml water and the combination extracted with three 250 ml portions of methylene chloride. The combined methylene chloride extract was washed with two 250 ml portions of water, dried over magnesium sulfate and evaporated under reduced pressure. The residue was dissolved in benzene and chromatographed with acetone-benzene on a 300 g column of florisil packed in benzene. Starting material, 1.6 g., was recovered in the benzene elution and 3.6 g. containing the product as free base was obtained from the acetone-benzene elution on evaporation of solvent. A portion of the crude free base, 2.5 g., was dissolved in hot isopropyl alcohol and reacted with 0.8 g (0.0064 mole) of oxalic acid dihydrate. The oxalate salt, which precipitated on cooling, was collected by filtration and recrystallized from ethanol to give 2.2 g product, m.p. 206°–208° C. Drying conditions prior to analyses were: 5 hr at 97°–98° C./0.02 mm Hg; over night at room temperature/0.02 mm Hg.

Analysis: Calculated for $C_{25}H_{25}ClN_4O_4$: C,62.43; H,5.24; N, 11.65. Found: C,62.52; H,5.23; N,11.76.

EXAMPLE 9

N,N-Dimethyl-6-phenyl-11H-pyrido[2,3-b][1,4]benzodiazepine-11-propanamine fumarate [1:1]

To a stirred suspension of 1.68 g (0.070 mole) of sodium hydride (in mineral oil) in 25 ml of anhydrous dimethylformamide, under nitrogen atmosphere, was added, portionwise, a suspension of 8.0 g (0.029 mole) of 6-phenyl-11H-pyrido[2,3-b][1,4]benzodiazepine in 20 ml of anhydrous dimethylformamide. The mixture was stirred for 30 min after addition was complete, warmed to 65° C. for 15 min and cooled again to room temperature. To the mixture was added 5.6 g (0.035 mole) of 3-dimethylaminopropyl chloride hydrochloride. After stirring overnight at room temperature, thin-layer chromatography indicated the reaction was nearly completed. The reaction mixture was poured into 1500 ml water and extracted with 250 ml of methylene chloride. The methylene chloride extract was washed with three 250 ml portions of water, dried over magnesium sulfate and evaporated under reduced pressure. The residue was dissolved in methylene chloride and extracted with 100 ml and 150 ml portions of 3 N hydrochloric acid. Unreacted 6-phenyl-11H-pyrido[2,3-b][1,4]benzodiazepine starting material precipitated from the aqueous acidic solution and was separated by carefully decanting the liquid from the solid. The aqueous solution was basified with 3 N sodium hydroxide and extracted with three 100 ml portions of methylene chloride. The combined methylene chloride extracts were dried over magnesium sulfate and evaporated under reduced pressure to give 7.7 g residue, the free base of the title compound. A solution of 6.6 g of the residue in hot isopropyl alcohol was reacted with 2.15 g of fumaric acid and the mixture heated until dissolution was completed. On standing for 48 hr, the salt which had precipitated was collected by filtration. After recrystallization from isopropyl alcohol-isopropyl ether, 5.9 g of product was obtained, m.p. 171°–173° C. Drying conditions prior to analyses were: 4 hr at 90° C./0.1 mm Hg; overnight at room temperature/0.1 mm Hg.

Analysis: Calculated for $C_{27}H_{28}N_4O_4$: C,68.73; H,5.97; N,11.86. Found: C,68.37; H,6.05; N,11.73.

EXAMPLE 10

N,N-Dimethyl-6-phenyl-11H-pyrido[2,3-b][1,4]benzodiazepin-11-ethanamine fumarate [1:1]

To a stirred suspension of 1.48 g (0.062 mole) of sodium hydride (in mineral oil) in 35 ml of anhydrous dimethylformamide, under nitrogen atmosphere, was added, portionwise, 7.0 g (0.026 mole) of 6-phenyl-11H-pyrido[2,3-b][1,4]benzodiazepine. Aftr cooling the reaction mixture to room temperature, 4.46 g (0.031 mole) of 2-dimethylaminoethyl chloride hydrochloride was added portionwise and stirring continued overnight. The reaction mixture was poured into 1500 ml of water and the resultant mixture extracted with 250 ml of methylene chloride. The methylene chloride extract was washed with three 500 ml portions of water, dried over magnesium sulfate and evaporated under reduced pressure to give 8.6 g of an oil, the free base of the title compound. Part of the oil, 6.9 g, was reacted with an equal molar amount of fumaric acid in isopropyl alcohol. Addition of isopropyl ether gave an oily solid. The mixture was evaporated under reduced pressure and the residue crystallized on standing. The crystals were triturated with acetone and recrystallized from acetone-isopropyl ether to give 4.3 g of the fumarate salt, m.p. 175°–177.5° C.

Analysis: Calculated for $C_{26}H_{26}N_4O_4$: C,68.11; H,5.72; N,12.22. Found: C,67.88; H,5.72; N,12.17.

EXAMPLE 11

11-[3-(4-Morpholinyl)propyl]-6-phenyl-11H-pyrido[2,3-b][1,4]benzodiazepine fumarate [1:1]

To a stirred suspension of 1.10 g (0.046 mole) of sodium hydride (in mineral oil) in 25 ml of anhydrous dimethylformamide under nitrogen pressure was added, portionwise, 5.0 g (0.0184 mole) of 6-phenyl-11H-pyrido[2,3-b][1,4]benzodiazepine. The reaction mixture was stirred at room temperature for 15 min, warmed at 65°–70° C. for 10 min and allowed to cool to room temperature. To the mixture was added, portionwise, 4.1 g (0.02 mole) of 4-(3-chloropropyl)morpholine hydrochloride. The reaction mixture was stirred at room temperature for 16 hr and then poured into 800 ml of water. This mixture was extracted twice with 200 ml portions of methylene chloride. The combined methylene chloride extracts were extracted with 150 ml and 75 ml portions of 3 N hydrochloric acid and the combined aqueous extracts were basified with 3 N sodium hydroxide. The resulting suspension was extracted with two 150 ml portions of methylene chloride and these latter two extracts combined, dried over magnesium sulfate and evaporated under reduced pressure. The residue, the free base of the title compound, was reacted with an equal molar amount of fumaric acid in warm isopropyl alcohol and the mixture treated with isopropyl ether. The fumarate salt was collected by filtration and recrystallized from ethanol-ethyl acetate to give 5.6 g, m.p. 154°–7° C. Drying conditions prior to analyses were: 4 hr at 97°–98° C./0.1 mm Hg; overnight at room temperature/0.1 mm Hg.

Analysis: Calculated for $C_{29}H_{30}N_4O_5$: C,67.69; H,5.88; N,10.88. Found: C,67.52; H,5.84; N,10.90.

EXAMPLE 12

N,N-Diethyl-6-phenyl-11H-pyrido[2,3-b][1,4]benzodiazepine-11-propanamine oxalate [1:1]

To a stirred suspension of 1.10 g (0.0461 mole) of sodium hydride (in mineral oil) in 25 ml of anhydrous dimethylformamide under nitrogen atmosphere was added, portionwise, 5.0 g (0.0184 mole) of 6-phenyl-11H-pyrido[2,3-b][1,4]benzodiazepine. The reaction mixture was stirred at room temperature for 0.5 hr, warmed to 65°–70° C. and cooled slowly to room temperature. To the mixture was added, portionwise, 3.77 g (0.020 mole) of 3-diethylaminopropylchloride hydrochloride and the reaction mixture stirred at room temperature for 16 hr. The mixture was poured into 750 ml of water and extracted with three 150 ml portions of methylene chloride. The combined methylene chloride extracts were extracted with 150 ml and 75 ml portions of 3 N hydrochloric acid. The combined aqueous extracts were basified with 3 N sodium hydroxide and then extracted with three 100 ml portions of methylene chloride. The combined methylene chloride extracts were dried over magnesium sulfate and evaporated under reduced pressure to give 7.5 g of the free base of the title compound. A portion, 5.6 g, was reacted with an equal molar amount of oxalic acid dihydrate in hot isopropyl alcohol. The oxalate salt was collected by filtration to give 5.5 g product, m.p. 196°–199° C. Drying conditions prior to analyses were: 1 hr at 97°–98° C./0.1 mm Hg.

Analysis: Calculated for $C_{27}H_{30}N_4O_4$: C,68.34; H,6.37; N,11.81. Found: C,68.31; H,6.43; N,11.86.

EXAMPLE 13

9-Chloro-N,N-dimethyl-6-phenyl-11H-pyrido[2,3-b][1,4]benzodiazepine-11-propanamine fumarate [1:1]

To a stirred suspension of 0.98 g (0.041 mole) of sodium hydride (in mineral oil) in 25 ml of anhydrous dimethylformamide under nitrogen atmosphere was added, portionwise, 5.0 g (0.016 mole) of 9-chloro-6-phenyl-11H-pyrido[2,3-b][1,4]benzodiazepine over a 45 min period. The reaction mixture was stirred at room temperature for 1 hr, warmed to 70° C. and then cooled slowly to room temperature. To the mixture was added, portionwise, over a 30 min period, 2.84 g (0.018 mole) of 3-dimethylaminopropyl chloride hydrochloride and the reaction mixture stirred at room temperature for 17 hr. The mixture was poured into 750 ml water and extracted with 150 ml and two 100 ml portions of methylene chloride. The combined methylene chloride extracts were washed with two 100 ml portions of water followed by extraction with 100 ml and 75 ml portions of 3 N hydrochloric acid. The acidic extracts were combined and filtered to remove precipitate which had formed and the filtrate was basified with 3 N sodium hydroxide and extracted with three 100 ml portions of methylene chloride. The combined methylene chloride extracts were dried over magnesium sulfate and evaporated under reduced pressure. The residue was dissolved in methylene chloride and filtered through a 50–60 g bed of florisil in a sintered glass funnel. The bed was washed in succession with 1%, 2%, 3% and 5% methanol-methylene chloride mixtures, the filtrates combined and evaporated under reduced pressure to give the free base of the title compound. The free base was reacted with an equal molar amount of fumaric acid in hot isopropanol to give 3.3 g fumarate, m.p. 199°–202° C.

Analysis: Calculated for $C_{27}H_{27}N_4O_4Cl$: C,63.96; H,5.37; N,11.05. Found: C,63.63; H,5.36; N,11.00.

EXAMPLE 14

6-Phenyl-11-[3-(1-piperidinyl)propyl]-11H-pyrido[2,3-b][1,4]benzodiazepine fumarate [1:1]

To a stirred suspension of 1.10 g (0.0461 mole) of sodium hydride (in mineral oil) in 25 ml of anhydrous dimethylformamide under nitrogen atmosphere was added, portionwise, 5.0 g (0.018 mole) of 6-phenyl-11H-pyrido[2,3-b][1,4]benzodiazepine. The reaction mixture was stirred for 30 min, warmed to 70° C. and cooled to room temperature. To the mixture was added, portionwise, 4.14 g (0.0203 mole) of N-(3-chloropropyl)piperidine hydrochloride and the reaction mixture was stirred at room temperature for 16 hr. The mixture was poured into 750 ml of water, extracted with 150 ml methylene chloride by stirring for 15 min. The aqueous layer was extracted with two additional 100 ml portions of methylene chloride. The combined methylene chloride extracts were extracted with 150 ml and 75 ml portions of 3 N hydrochloric acid and the combined acid extracts basified with 3 N sodium hydroxide and then extracted with three 100 ml portions of methylene chloride. The methylene chloride extracts were combined, dried over magnesium sulfate and evaporated under reduced pressure. The residue was dissolved in a minimum of methylene chloride and filtered through a 100 g bed of florisil in a sintered glass funnel. The bed was washed successively with methylene chloride, 1%, 2%, 3% and 5% methanol-methylene chloride mixtures. All the filtrates were combined and evaporated under reduced pressure. The residue was reacted with 1.3 g fumaric acid in hot isopropanol and isopropyl ether added. An amorphous precipitate was formed. The entire mixture was evaporated to dryness and the residue dissolved in 200 ml of ethanol. The solution was warmed to reflux, filtered and isopropyl ether added to the filtrate. Crystals which formed overnight are filtered off to give 4.1 g fumarate salt, m.p. 153°–6° C. Drying conditions prior to analyses were: 4 hr at 97°–98° C./0.1 mm Hg.

Analysis: Calculated for $C_{30}H_{32}N_4O_4$: C,70.29; H,6.29; N,10.93. Found: C,70.38; H,6.32; N,10.92.

EXAMPLE 15

6-(4-Chlorophenyl)-N,N-dimethyl-11H-pyrido[2,3-b][1,4]benzodiazepine-11-propanamine fumarate [1:1]

To a stirred suspension of 1.57 g (0.065 mole) of sodium hydride (in mineral oil) in 25 ml of anhydrous dimethylformamide was added under nitrogen atmosphere, 8.0 g (0.026 mole) of 6-(4-chlorophenyl)-11H-pyrido[2,3-b][1,4]benzodiazepine. The reaction mixture was stirred for 1 hr at room temperature, warmed at 80° C. for 15 min and cooled to room temperature. To the mixture was added, portionwise, 4.55 g (0.029 mole) of 3-dimethylaminopropyl chloride hydrochloride and the mixture was stirred overnight at room temperature. The mixture was poured into 750 ml of water and stirred for 30 min with 150 ml of methylene chloride. The aqueous layer was extracted further with three 100 ml portions of methylene chloride. The combined methylene chloride extracts were dried over magnesium sulfate and evaporated under reduced pressure to give the free base of the title compound. The free base was reacted with an equal molar amount of fumaric acid in hot isopropanol. On cooling, 3.6 g of the fumarate salt precipitated, m.p. 200.5°–202.5° C. The product was air dried further prior to analysis.

Analysis: Calculated for $C_{27}H_{27}ClN_4O_4$: C,63.96; H,5.37; N,11.05. Found: C,64.18; H,5.33; N,11.07.

EXAMPLE 16

8-Chloro-N,N-dimethyl-6-phenyl-11H-pyrido[2,3-b][1,4]-benzodiazepin-11-ethanamine oxalate [1:1]

To a stirred suspension of 1.05 g (0.044 mole) of sodium hydride (in mineral oil) in 50 ml of anhydrous dimethylformamide was added, portionwise, 6.1 g (0.02 mole) of 8-chloro-6-phenyl-11H-pyrido[2,3-b][1,4]benzodiazepine. The reaction mixture was stirred at room temperature for 1.5 hr, during which time evolution of hydrogen ceased. The reaction mixture was cooled to 5° C. and 3.2 g (0.022 mole) of 2-dimethylaminoethyl chloride hydrochloride was added, portionwise, followed by stirring at toom temperature for about 60 hr. The reaction mixture was poured into 1600 ml of water and the mixture extracted three times with 500 ml portions of methylene chloride. The combined extracts were washed with two 500 ml portions of water, dried over magnesium sulfate and evaporated under reduced pressure. Thin layer chromatography (20% methanol/benzene on silica gel) indicated the presence of free base of the title compound and of starting material. The residue was dissolved in benzene and chromatographed on a 200 g column of florisil packed in benzene. Starting material, 1.3 g of 8-chloro-6-phenyl-11H-pyrido[2,3-b][1,4]benzodiazepine was eluted with benzene and the free base of the title compound was eluted with mixtures of acetone in benzene. The free base was reacted with an equal molar amount of oxalic acid dihydrate in refluxing isopropyl alcohol and product recrystallized from isopropyl alcohol weighed 1.6 g, m.p. 228°-5°-232° C. Drying conditions prior to analysis were 6 hr at 82° C./0.1 mm Hg; overnight at room temperature.

Analysis: Calculated for $C_{24}H_{23}ClN_4O_4$: C,61.74; H,4.96; N,12.00. Found: C,61.62; H,4.95; N,11.98.

EXAMPLE 17

8-Chloro-11-methyl-6-phenyl-11H-pyrido[2,3-b][1,4]benzodiazepine

To a stirred suspension of 0.25 g (0.01 mole) of sodium hydride (in mineral oil) in 15 ml of anhydrous dimethylformamide was added, portionwise, 3.05 g (0.01 mole) of 8-chloro-6-phenyl-11H-pyrido[2,3-b][1,4]benzodiazepine. The mixture was warmed at about 60° C. for one hr. A solution of 1.42 g (0.01 mole) of methyl iodide in 10 ml of anhydrous dimethylformamide was added dropwise over a 0.5 hr period and the reaction mixture stirred overnight at room temperature after which it was poured into 400 ml of water and stirred for 2 hr. The precipitated solid was recrystallized twice from isopropyl alcohol to give 2.0 g of product, m.p. 153°-6° C. Drying conditions prior to analyses were 1 hr at 82° C./0.1 mm Hg.

Analysis: Calculated for $C_{19}H_{14}ClN_3$: C,71.36; H,4.41; N,13.14. Found: C,71.64; H,4.43; N,13.32.

EXAMPLE 18

N,N-Dimethyl-6-(4-methylphenyl)-11H-pyrido[2,3-b][1,4]benzodiazepine-11-propanamine fumarate [1:1]

To a stirred suspension of 0.51 g (0.022 mole) of sodium hydride in 25 ml of anhydrous dimethylformamide under nitrogen atmosphere was added, portionwise, 4.2 g (0.0147 mole) of 6-(4-methylphenyl)-11H-pyrido[2,3-b][1,4]benzodiazepine over a 45 min period. The mixture was stirred for 1 hr at room temperature, warmed at 75°-80° C. for 1 hr, cooled to room temperature and a solution of 0.0184 mole of 3-dimethylaminopropyl chloride in 10 ml of anhydrous dimethylformamide was added dropwise. The mixture was stirred overnight at room temperature and poured into 1000 ml of water. The suspension was extracted with three 150 ml portions of methylene chloride and the combined methylene chloride extracts were extracted with two 150 ml portions of 3 N hydrochloric acid. A precipitate formed in the acidic solution which was removed by filtration and discarded. The filtrate was basified with 3 N NaOH and extracted with three 100 ml portions of methylene chloride. The combined methylene chloride extracts were dried over magnesium sulfate and evaporated under reduced pressure to give an oil, the free base of the title compound. This residual oil was dissolved in hot isopropyl alcohol and reacted with an equal molar amount of fumaric acid. The fumarate salt crystallized as the solution cooled to room temperature and was recrystallized twice from isopropyl alcohol-isopropyl ether to give 1.7 g product, m.p. 187°-189° C., (decomp.).

Analysis: Calculated for $C_{28}H_{30}N_4O_4$: C,69.12; H,6.22; N,11.52. Found: C,68.86; H,6.32; N,11.36.

EXAMPLE 19

6-(4-Methoxyphenyl)-N,N-dimethyl-11H-pyrido[2,3-b][1,4]benzodiazepine-11-propanamine fumarate [1:1]

To a stirred suspension of 0.45 g (0.0187 mole) of sodium hydride in 25 ml of anhydrous dimethylformamide under nitrogen atmosphere was added 4.5 g (0.015 mole) of 6-(4-methoxyphenyl)-11H-pyrido[2,3-b][1,4]benzodiazepine over a 30 min period. The mixture was stirred for 30 min at room temperature followed by warming at 80°-90° C. for one hr, cooling to room temperature and a solution of 0.019 mole of 3-dimethylaminopropyl chloride in 5 ml of anhydrous dimethylformamide was added dropwise. The reaction mixture was stirred overnight at room temperature and poured into 800 ml of water. The suspension was extracted with two 150 ml portions of methylene chloride. The combined extracts were washed with 500 ml of water then extracted with two 100 ml portions of 3 N hydrochloric acid. The solid which precipitated from the combined acidic extracts was filtered off and discarded. The filtrate was basified with 3 N sodium hydroxide and extracted with three 100 ml portions of methylene chloride. The combined methylene chloride extracts were dried over magnesium sulfate and evaporated under reduced pressure. The residual oil had partially crystallized and was triturated in methylene chloride and filtered, leaving in a residue of 0.32 g. The filtrate was evaporated under reduced pressure and the residual oil triturated in hot benzene and filtered, leaving a residue of 0.8 g. The benzene filtrate was evaporated under reduced pressure and the residual oil was reacted with 1.02 g fumaric acid in hot isopropyl alcohol. Upon cooling, an oil separated from solution. The supernatant liquid was decanted and the oil seeded. After crystallizing partially, the mixture was filtered to give 2.5 g solid, m.p. 157°-60° C. An attempted recrystallization from isopropyl alcohol-isopropyl ether again produced an oil-solid mixture. The mixture was reheated with additional isopropyl alcohol, solubilized, filtered, seeded and cooled. The fumarate salt precipitated and was collected by filtering to give 2.0 g, m.p. 159°-161° C.

Analysis: Calculated for $C_{28}H_{30}N_4O_5$: C,66.92; H,6.02; N,11.15. Found: C,66.90; H,6.08; N,11.08.

EXAMPLE 20

6-(3-Chlorophenyl)-11H-pyrido[2,3-b][1,4]benzodiazepine

A mixture of 14 g (0.0433 mole) of [2-[(3-amino-2-pyridinyl)amino]phenyl](3-chlorophenyl)-methanone and 0.3 g of para toluene sulfonic acid in 500 ml of toluene were heated at reflux overnight using a Dean-Stark trap to collect water. At the end of the reflux time, some of the toluene (ca 250 ml) was distilled off and the hot solution was filtered. Pet. ether (30°-60° C.) was added to the cloud point. The solution was refrigerated overnight and filtered to give, after air drying, 10 g (76%) gold colored crystals. A portion was recrystallized from isopropyl alcohol-isopropyl ether, m.p. 160°-160.5° C.

Analysis: Calculated for $C_{18}H_{12}N_3Cl$: C,70.71; H,3.96; N,13.74. Found: C,70.47; H,3.98; N,13.62.

EXAMPLE 21

6-(3-Chlorophenyl)-N,N-dimethyl-11H-pyrido[2,3-b][1,4]benzodiazepine-11-propanamine fumarate [1:1]

To a stirred suspension of 3.4 g (0.07 mole) of sodium hydride (in mineral oil) in 250 ml of anhydrous dimethylformamide was added under nitrogen atmosphere in portions 8.5 g (0.028 mole) of 6-(3-chlorophenyl)-11H-pyrido[2,3-b][1,4]benzodiazepine. The mixture was stirred for 30 min at room temperature. The temperature was raised to 80° C. for 3 hr and thereafter allowed to cool to room temperature. To the reaction mixture was added dropwise a solution of 4.9 g (0.031 mole) of 3-dimethylaminopropyl chloride hydrochloride in 30 ml of dimethylformamide over a 20 minute period. the reaction mixture was allowed to stir at room temperature overnight under nitrogen atmosphere. Thin layer chromatography indicated some starting material was present. Additional sodium hydride 1.4 g (0.03 mole) was added and after 15 min 4.7 g (0.03 mole) of 3-dimethylaminopropyl chloride hydrochloride was added followed by stirring for 4½ hr. Water (20 ml) was added dropwise and the reaction mixture filtered and concentrated on a rotary evaporator. The residue was partitioned between diethyl ether and dilute sodium hydroxide. The ether layer was washed with water 3 times and extracted with dilute aqueous hydrochloric acid. The water layer was basified with sodium hydroxide pellets and extracted with methylene chloride. The methylene chloride layer was dried and concentrated to give a residue of 7.5 g product. The free base was reacted with fumaric acid and the fumarate salt recrystallized from ethyl acetate-ethanol, m.p. 167.5°–168.5° C.

Analysis: Calculated for $C_{23}H_{23}N_4Cl$: C,63.96; H,5.47; N,11.05. Found: C,63.95; H,5.39; N,11.00.

EXAMPLE 22

6-(4-Fluorophenyl)-11H-pyrido[2,3-b][1,4]benzodiazepine

A mixture of 11.5 g (0.037 mole) of [2-[(3-amino-2-pyridinyl)amino]phenyl](4-fluorophenyl)methanone and 0.6 g of para toluene sulfonic acid in toluene was refluxed for 24 hr using a Dean-Stark trap to collect water. At the end of reflux, some of the toluene (300 ml) was distilled off and the hot solution was filtered. Pet.-ether (30°–60°) was added to cloud point. The solution was refrigerated overnight (0° C.) and filtered to give 10.7 g crystals. A portion of the material was recrystallized from isopropyl alcohol and dried in vacuo overnight at 65° C., m.p. 203°–205° C.

Analysis: Calculated for $C_{18}H_{12}N_3F$: C,74.73; H,4.18; N,14.52. Found: C,74.61; H,4.17; N,14.54.

EXAMPLE 23

6-(4-Fluorophenyl)-N,N-dimethyl-11H-pyrido[2,3-b][1,4]benzodiazepine-11-propanamine hydrochloride hemihydrate To a stirred suspension of 3.6 g (0.075 mole) of sodium hydride (in mineral oil) in 250 ml of anhydrous dimethylformamide was added under nitrogen atmosphere in portions 8.7 g (0.03 mole) of 6-(4-fluorophenyl)-11H-pyrido[2,3-b][1,4]benzodiazepine. The mixture was stirred for 30 min at room temperature. The temperature was raised to 80° C. for 3.5 hr. and thereafter allowed to cool to 45° C. To the reaction mixture was added dropwise a solution of 5.2 g (0.033 mole) of 3-dimethylaminopropyl chloride hydrochloride in 30 ml of dimethylformamide. After stirring overnight at room temperature, thin layer chromatography indicated the presence of starting material. Additional sodium hydride, 3.6 g (0.075 mole) was added and after 45 min stirring, the reaction mixture was heated to 50°–60° C. for ½ hr. A green color developed with formation of gas. The mixture was stirred at room temperature for 3 hr. A solution of 5.2 g (0.033 mole) of 3-dimethylaminopropyl chloride in 30 ml of dimethylformamide was added dropwise. (About half way through the addition, a green color developed and addition was halted temporarily for about an hour). The reaction mixture was stirred overnight at room temperature. To the mixture was added 30 ml of water while cooling. After gas evolution had stopped the mixture was filtered and concentrated in a rotary evaporator. The residue was partitioned between diethyl ether and water and the ether layer extracted with dilute aqueous hydrochloric acid solution. The aqueous layer was filtered after 1½ hr to remove solid. The filtrate was basified with sodium hydroxide pellets and extracted with methylene chloride. The extract was dried and concentrated. The residue was divided into two equal parts and purified by dry column chromatography on two 20″×1½″ columns of silica gel which had been deactivated by the development solvent (10% methanol, 1% concentrated ammonium hydroxide, 89% methylene chloride). The center portion of the column was cut out and extracted with the development solvent. The combined extracts were concentrated under reduced pressure and the residue dissolved in ethyl acetate-ethanol mixture and acidified with concentrated hydrochloric acid. The hydrochloric acid salt was recrystallized from ethanol-ethyl acetate mixture. The solid obtained by filtration was dried at 99° C. for 48 hr to give the title compound as the monohydrochloride hemihydrate, m.p. 120°–123° C.

Analysis: Calculated for $C_{46}H_{50}N_8F_2Cl_2O$: C,65.78; H,6.00 N,13.34. Found: C,65.58; H,5.77; N,13.47.

EXAMPLE 24

11-[3-(1,3-Dihydro-1,3-dioxo-2H-isoindol-2-yl)propyl]-6-phenyl-11H-pyrido[2,3-b][1,4]benzodiazepine To a stirred suspension of 0.56 g (0.023 mole) of sodium hydride in 25 ml of anhydrous dimethylformamide was added, portionwise, 5.0 g (0.0184 mole) of 6-phenyl-11H-pyrido[2,3-b][1,4]benzodiazepine. The reaction mixture was warmed to 80°±2° C. for 1 hr and cooled to room temperature. A solution of 5.55 g (0.020 mole) of N-(3-bromopropyl) phthalimide in 10 ml of anhydrous dimethylformamide was added dropwise and after stirring for 16 hr the reaction mixture was poured into 650 ml of water and stirred for 30 min. The yellow solid was collected by filtration and recrystallized three times from isopropyl alcohol to give 3.7 g of product, m.p. 170°–172° C.

Analysis: Calculated for $C_{29}H_{22}N_4O_2$: C,75.97; H,4.84; N,12.22. Found: C,76.25; H,4.87; N,12.34.

EXAMPLE 25

6-Phenyl-11H-pyrido[2,3-b][1,4]benzodiazepine-11-propanamine, dihydrochloride, hemihydrate A mixture of 16.2 g (0.035 mole) of 6-phenyl-11-[3-(phthalimido)propyl]-11H-pyrido[2,3-b][1,4]benzodiazepine and 2.29 g (0.0387 mole) of hydrazine hydrate, 85% in 175 ml of 190 proof ethyl alcohol was refuxed for 2.5 hr and allowed to stand for 72 hr. A solution of 10 ml conc. hydrochloric acid in 50 ml of water was added to the mixture. The mixture was stirred overnight. The solid precipitate was collected by filtration and discarded. The filtrate was evaporated under reduced pressure. The residue, slightly wet, was suspended in 200 ml of water, the mixture was stirred for 2 hr and filtered through celite. The filtrate was evaporated under reduced pressure and the residue suspended in 100 ml of 200 proof ethyl alcohol and evaporated under reduced pressure. The latter procedure was repeated. The crude, damp residue (42.1 g) was recrystallized from isopropanol with standing for about 15 hr. The solid, collected by filtration, was dried at 82° over phosphorus anhydride at 0.1 mm Hg. for 3 hr; m.p. 210°–220° C. (decomp.).

Analysis: Calculated for $C_{42}H_{46}Cl_4N_8O$: C,61.47; H,5.65; N,13.65. Found: C,61.36; H,5.72; N,13.90.

EXAMPLE 26

6-Phenyl-11H-pyrido[2,3-b][1,4]benzodiazepine-11-propanamine

A portion of the 6-phenyl-11-pyrido[2,3-b][1,4]benzodiazepine-11-propanamine, dihydrochloride hemihydrate obtained in Example 25 was dissolved in water, basified with dilute sodium hydroxide, and extracted with three portions of methylene chloride. The combined methylene chloride extracts were filtered through a 50–60 g bed of florisil in a sintered glass funnel. The bed was washed in succession with 1%, 2%, 3% and 5% methanol-methylene chloride mixtures, the filtrates combined and evaporated under reduced pressure to give the free base, the title compound.

EXAMPLE 27

N-[3-[6-Phenyl-11H-pyrido[2,3-b][1,4]benzodiazepin-11-yl]propyl]methanimidic acid ethyl ester A solution of 8.8 g (0.021 mole) of 6-phenyl-11H-pyrido [2,3-b][1,4]bezodiazepine-11-propanamine in 150 ml of triethylorthoformate was heated at reflux for 4½ hr and allowed to stand overnight. The mixture was concentrated in vacuo, the residue was washed with pet-ether (30°–60° C.). Chemical ionization mass spec indicated the product was a mixture containing the title compound.

EXAMPLE 28

N-Methyl-6-phenyl-11H-pyrido[2,3-b][1,4]benzodiazepine-11-propanamine, dihydrochloride Preparation of Imidate Ester

[Procedure of Crochet, T. A. & Blanton, C. D., Jr. Synthesis 1974 (1) 55–56]

6-Phenyl-11H-pyrido[2,3-b][1,4]benzodiazepine-11-propanamine dihydrochloride hemihydrate, 25 g (0.06 mole) from Example 25 was converted to the free base by partitioning between dilute sodium hydroxide and methylene chloride, drying and concentrating the methylene chloride layer to dryness, adding dry benzene and again concentrating to drive off the benzene. The resulting free base was dissolved in 300 ml (267 g; 1.8 mole) of freshly distilled triethyl orthoformate with refluxing for 9 hr. The mixture was concentrated in vacuo, ethanol was added and the mixture concentrated again.

CONVERSION OF AMIDATE TO AMINE

The 23.4 g (0.061 mole) amidate prepared in the foregoing was dissolved in 200 ml of ethanol and sodium borohydrate added with stirring at 15°–20° C. until thin layer chromatography indicated reaction was essentially complete as indicated by absence of substantial starting material. Fifty ml of water was added slowly with stirring and cooling continued 15 min after the water addition. The mixture was then flooded with 2 liters of water and extracted with ethyl acetate. The ethyl acetate layer was washed with water until neutral wash was obtained and then saturated with sodium chloride. The resulting ethyl acetate layer was dried and concentrated. Diethyl ether was added and the mixture chilled. Some insoluble material was filtered off and discarded. The ether layer was concentrated and the product chromatographed on an alumina column (neutral, activity-1) eluting with ethyl acetate+methanol+traces of triethyl amine. The fractions containing substantial product (TLC) were partitioned between ethyl acetate and aqueous sodium hydroxide. Ethereal hydrogen chloride was added to the ethyl acetate layer and the crystalline product recrystallized from acetonitrile-water mixture. Melting point of the product was 139°–141° C.

Analysis: Calculated for $C_{22}H_{24}N_4Cl_2$: C,63.62; H,5.82; N,13.49. Found: C,63.81; H,6.15; N,13.60.

EXAMPLE 29

N-[3-[6-Phenyl-11H-pyrido[2,3-b][1,4]benzodiazepine-11-yl]propyl]carbamic acid ethyl ester To a solution of 1.6 g (0.0045 mole) of 6-phenyl-11H-pyrido[2,3-b][1,4]benzodiazepine-11-propanamine in dry methylene chloride was added 0.53 g (0.0052 mole) of triethylamine. To this solution was added dropwise, while cooling, 0.54 g (0.0050 mole) of ethyl chloroformate. The mixture was stirred at room temperature for 2 hr. The methylene chloride solution of the product (as indicated by chemical ionization mass spec) was washed with dilute sodium hydroxide-sodium chloride saturated aqueous solution and dried and concentrated to dryness. The residue was triturated in isopropyl ether. Yield was 1.5 g of title product.

EXAMPLE 30

5,6-Dihydro-N,N-dimethyl-6-phenyl-11H-pyrido[2,3-b][1,4]benzodiazepine-11-propanamine, dihydrochloride hemihydrate A solution of 3.0 g (0.0064 mole) of N,N-dimethyl-6-phenyl-11H-pyrido[2,3-b][1,4]benzodiazepine-11-propanamine in absolute methanol was adjusted to pH 5.6 with methanolic hydrogen chloride solution. To this solution was added at one time, 0.7 g (0.011 mole) of $NaBH_3CN$ and the reaction mixture was refluxed for 20 min. The ethanol was removed in vacuo and the residue was partitioned between dilute sodium hydroxide and methylene chloride. The methylene chloride layer was dried over magnesium sulfate and concentrated to leave a residue which was twice crystallized from 2-propanol and isopropyl ether. A yellow solid, 1.6 g (57%) was obtained which loses its crystalline structure on heating starting at 156°–160° C. with decomposition at 180°–195° C.

Analysis: Calculated for $C_{46}H_{58}N_8OCl_4$: C,62.73; H,6.64; N,12.72. Found: C,62.40; H,6.90 N,12.61.

EXAMPLES 31a TO 31r

Following the procedure of Example 6, the following methanone compounds:

[2-[(3-amino-2-pyridinyl)amino]phenyl]-(4-ethyl-phenyl)methanone,
[2-[(3-amino-2-pyridinyl)amino]phenyl]-(4-isopropyl-phenyl)methanone,
[2-[(3-amino-2-pyridinyl)amino]phenyl]-(4-bromo-phenyl)methanone,
[2-[(3-amino-2-pyridinyl)amino]phenyl]-(4-fluoro-phenyl)methanone,
[2-[(3-amino-2-pyridinyl)amino]phenyl]-(4-ethoxy-phenyl)methanone,
[2-[(3-amino-2-pyridinyl)amino]phenyl]-(4-nitro-phenyl)methanone,
[2-[(3-amino-2-pyridinyl)amino]phenyl]-(4-trifluorome-thylphenyl)methanone,
[2-[(3-amino-2-pyridinyl)amino]phenyl]-(3-methyl-phenyl)methanone,
[2-[(3-amino-2-pyridinyl)amino]phenyl]-(3-ethyl-phenyl)methanone,
[2-[(3-amino-2-pyridinyl)amino]phenyl]-(3-methoxy-phenyl)methanone,
[2-[(3-amino-2-pyridinyl)amino]phenyl]-(3-ethoxy-phenyl)methanone,
[2-[(3-amino-2-pyridinyl)amino]phenyl]-(2-nitro-phenyl)methanone,
[2-[(3-amino-2-pyridinyl)amino]phenyl]-(3-trifluorome-thylphenyl)methanone,
2-[(3-amino-2-pyridinyl)amino]phenyl]-(2-methyl-phenyl)methanone,
[2-[(3-amino-2-pyridinyl)amino]phenyl]-(2-ethyl-phenyl)methanone,
[2-[(3-amino-2-pyridinyl)amino]phenyl]-(2-methoxy-phenyl)methanone,
[2-[(3-amino-2-pyridinyl)amino]phenyl]-2,4-dichloro-phenyl)methanone, and
[2-[(3-amino-2-pyridinyl)amino]phenyl]-(3,4,5-trime-thoxyphenyl)methanone,
are cyclized to the following pyridobenzodiazepines:
(a) 6-(4-ethylphenyl)-11H-pyrido[2,3-b][1,4]ben-zodiazepine,
(b) 6-(4-isopropylphenyl)-11H-pyrido[2,3-b][1,4]ben-zodiazepine,
(c) 6-(4-bromophenyl)-11H-pyrido[2,3-b][1,4]ben-zodiazepine,
(d) 6-(4-fluorophenyl)-11H-pyrido[2,3-b][1,4]ben-zodiazepine,
(e) 6-(4-ethoxyphenyl)-11H-pyrido[2,3-b][1,4]ben-zodiazepine,
(f) 6-(4-nitrophenyl)-11H-pyrido[2,3-b][1,4]ben-zodiazepine,
(g) 6-(4-trifluoromethylphenyl)-11H-pyrido[2,3-b][1,4]benzodiazepine,
(h) 6-(3-methylphenyl)-11H-pyrido[2,3-b][1,4]ben-zodiazepine,
(i) 6-(3-ethylphenyl)-11H-pyrido[2,3-b][1,4]ben-zodiazepine,
(j) 6-(3-methoxyphenyl)-11H-pyrido[2,3-b][1,4]ben-zodiazepine,
(k) 6-(3-ethoxyphenyl)-11H-pyrido[2,3-b][1,4]ben-zodiazepine,
(l) 6-(2-nitrophenyl)-11H-pyrido[2,3-b][1,4]ben-zodiazepine,
(m) 6-(3-trifluoromethylphenyl)-11H-pyrido[2,3-b][1,4]benzodiazepine,
(n) 6-(2-methylphenyl)-11H-pyrido[2,3-b][1,4]ben-zodiazepine,
(o) 6-(2-ethylphenyl)-11H-pyrido[2,3-b][1,4]ben-zodiazepine,
(p) 6-(2-methoxyphenyl)-11H-pyrido[2,3-b][1,4]ben-zodiazepine,
(q) 6-(2,4-dichlorophenyl)-11H-pyrido[2,3-b][1,4]benzodiazepine, and
(r) 6-(3,4,5-trimethoxyphenyl)-11H-pyrido[2,3-b][1,4]benzodiazepine.

EXAMPLES 32a TO 32o

Following the procedure of Example 3, the following methanone compounds:
[2-[(3-amino-2-pyridinyl)amino]-5-chlorophenyl](-phenyl)methanone,
[2-[(3-amino-2-pyridinyl)amino]-6-chlorophenyl](-phenyl)methanone,
[2-[(3-amino-2-pyridinyl)amino]-4-bromophenyl](-phenyl)methanone,
[2-[(3-amino-2-pyridinyl)amino]-4-fluorophenyl](-phenyl)methanone,
[2-[(3-amino-2-pyridinyl)amino]-4-trifluoromethyl-phenyl](phenyl)methanone,
[2-[(3-amino-2-pyridinyl)amino]-4-methylphenyl](-phenyl)methanone,
[2-[(3-amino-2-pyridinyl)amino]-5-methylphenyl](-phenyl)methanone,
[2-[(3-amino-2-pyridinyl)amino]-6-methylphenyl](-phenyl)methanone,
[2-[(3-amino-2-pyridinyl)amino]-4-ethylphenyl](-phenyl)methanone,
[2-[(3-amino-2-pyridinyl)amino]-4-methoxyphenyl](-phenyl)methanone,
[2-[(3-amino-2-pyridinyl)amino]-4-ethoxyphenyl](-phenyl)methanone,
[2-[(3-amino-2-pyridinyl)amino]-4-nitrophenyl](-phenyl)methanone,
[2-[(3-amino-2-pyridinyl)amino]-5-nitrophenyl](-phenyl)methanone,
[2-[(3-amino-2-pyridinyl)amino]-3-methylphenyl](-phenyl)methanone, and
[2-[(3-amino-2-pyridinyl)amino-3-chlorophenyl](-phenyl)methanone,
are cyclized to the following benzodiazepines:
(a) 8-chloro-6-phenyl-11H-pyrido[2,3-b][1,4]ben-zodiazepine,
(b) 7-chloro-6-phenyl-11H-pyrido[2,3-b][1,4]ben-zodiazepine,
(c) 9-bromo-6-phenyl-11H-pyrido[2,3-b][1,4]ben-zodiazepine,
(d) 9-fluoro-6-phenyl-11H-pyrido[2,3-b]1,4 ben-zodiazepine,
(e) 6-phenyl-9-trifluoromethyl-11H-pyrido[2,3-b][1,4]benzodiazepine,
(f) 9-methyl-6-phenyl-11H-pyrido[2,3-b][1,4]ben-zodiazepine,
(g) 8-methyl-6-phenyl-11H-pyrido[2,3-b][1,4]ben-zodiazepine,
(h) 7-methyl-6-phenyl-11H-pyrido[2,3-b][1,4]ben-zodiazepine,
(i) 9-ethyl-6-phenyl-11H-pyrido[2,3-b][1,4]ben-zodiazepine,
(j) 9-methoxy-6-phenyl-11H-pyrido[2,3-b][1,4]ben-zodiazepine,
(k) 9-ethoxy-6-phenyl-11H-pyrido[2,3-b][1,4]ben-zodiazepine,
(l) 9-nitro-6-phenyl-11H-pyrido[2,3-b][1,4]ben-zodiazepine,
(m) 8-nitro-6-phenyl-11H-pyrido[2,3-b][1,4]ben-zodiazepine, (n) 10-methyl-6-phenyl-11H-pyrido[2,3-b][1,4]benzodiazepine,
and
(o) 10-chloro-6-phenyl-11H-pyrido[2,3-b][1,4]benzodiazepine.

EXAMPLES 33a TO 33r

Utilizing the procedure of Example 15 but substituting equal molar amounts of each of the compounds prepared in Example 31, the following 6-phenyl-substituted pyridobenzodiazepines are prepared:
(a) 6-(4-ethylphenyl)-N,N-dimethyl-11H-pyrido[2,3-b][1,4]benzodiazepine-11-propanamine,
(b) N,N-dimethyl-6-[4-(1-methylethyl)phenyl]-11H-pyrido[2,3-b][1,4]benzodiazepine-11-propanamine,
(c) 6-(4-bromophenyl)-N,N-dimethyl-11H-pyrido[2,3-b][1,4]benzodiazepine-11-propanamine,
(d) 6-(4-fluorophenyl)-N,N-dimethyl-11H-pyrido[2,3-b][1,4]benzodiazepine-11-propanamine,
(e) 6-(4-ethoxyphenyl)-N,N-dimethyl-11H-pyrido[2,3-b][1,4]benzodiazepine-11-propanamine,
(f) N,N-dimethyl-6-(4-nitrophenyl)-11H-pyrido[2,3-b][1,4]benzodiazepine-11-propanamine,
(g) N,N-dimethyl-6-[4-(trifluoromethyl)phenyl]-11H-pyrido[2,3-b][1,4]benzodiazepine-11-propanamine,
(h) N,N-dimethyl-6-(3-methylphenyl)-11H-pyrido[2,3-b][1,4]benzodiazepine-11-propanamine,
(i) 6-(3-ethylphenyl)-N,N-dimethyl-11H-pyrido[2,3-b][1,4]benzodiazepine-11-propanamine,
(j) 6-(3-methoxyphenyl)-N,N-dimethyl-11H-pyrido[2,3-b][1,4]benzodiazepine-11-propanamine,
(k) 6-(3-ethoxyphenyl)-N,N-dimethyl-11H-pyrido[2,3-b][1,4]benzodiazepine-11-propanamine,
(l) N,N-dimethyl-6-(2-nitrophenyl)-11H-pyrido[2,3-b][1,4]benzodiazepine-11-propanamine,
(m) N,N-dimethyl-6-[4-(trifluoromethyl)phenyl]-11H-pyrido[2,3-b][1,4]benzodiazepine-11-propanamine,
(n) N,N-dimethyl-6-(2-methylphenyl)-11-pyrido[2,3-b][1,4]benzodiazepine-11-propanamine,
(o) 6-(2-ethylphenyl)-N,N-dimethyl-11H-pyrido[2,3-b][1,4]benzodiazepine-11-propanamine,
(p) 6-(2-methoxyphenyl)-N,N-dimethyl-11H-pyrido[2,3-b][1,4]benzodiazepine-11-propanamine,
(q) 6-(2,4-dichlorophenyl)-N,N-dimethyl-11H-pyrido[2,3-b][1,4]benzodiazepine-11-propanamine, and
(r) N,N-dimethyl-6-(3,4,5-trimethoxyphenyl)-11H-pyrido[2,3-b][1,4]benzodiazepine-11-propanamine.

EXAMPLES 34a TO 34o

Utilizing the procedure of Example 13 but substituting equal molar amounts of the compounds prepared in Example 32 for 9-chloro-6-phenyl-11H-pyrido[2,3-b][1,4]benzodiazepine, the following pyridobenzodiazepines are prepared:
(a) 8-chloro-N,N-dimethyl-6-phenyl-11H-pyrido[2,3-b][1,4]benzodiazepine-11-propanamine,
(b) 7-chloro-N,N-dimethyl-6-phenyl-11H-pyrido[2,3-b][1,4]benzodiazepine-11-propanamine,
(c) 9-bromo-N,N-dimethyl-6-phenyl-11H-pyrido[2,3-b][1,4]benzodiazepine-11-propanamine,
(d) 9-fluoro-N,N-dimethyl-6-phenyl-11H-pyrido[2,3-b][1,4]benzodiazepine-11-propanamine,
(e) N,N-dimethyl-6-phenyl-9-(trifluoromethyl)-11H-pyrido[2,3-b][1,4]benzodiazepine-11-propanamine,
(f) N,N9-trimethyl-6-phenyl-11H-pyrido[2,3-b][1,4]benzodiazepine-11-propanamine,
(g) N,N,8-trimethyl-6-phenyl-11H-pyrido[2,3-b][1,4]benzodiazepine-11-propanamine,
(h) N,N,7-trimethyl-6-phenyl-11H-pyrido[2,3-b][1,4]benzodiazepine-11-propanamine,
(i) 9-ethyl-N,N-dimethyl-6-phenyl-11H-pyrido[2,3-b][1,4]benzodiazepine-11-propanamine,
(j) 9-methoxy-N,N-dimethyl-6-phenyl-11H-pyrido[2,3-b][1,4]benzodiazepine-11-propanamine,
(k) 9-ethoxy-N,N-dimethyl-6-phenyl-11H-pyrido[2,3-b][1,4]benzodiazepine-11-propanamine,
(l) N,N-dimethyl-9-nitro-6-phenyl-11H-pyrido[2,3-b][1,4]benzodiazepine-11-propanamine,
(m) N,N-dimethyl-8-nitro-6-phenyl-11H-pyrido[2,3-b][1,4]benzodiazepine-11-propanamine,
(n) N,N-10,trimethyl-6-phenyl-11H-pyrido[2,3-b][1,4]benzodiazepine-11-propanamine, and
(o) 10-chloro-N,N-dimethyl-6-phenyl-11H-pyrido[2,3-b][1,4]benzodiazepine-11-propanamine.

EXAMPLES 35a TO 35c

Following the procedure of Example 1 and substituting equal molar amounts of the following for 3-amino-2-chloropyridine:
4-amino-3-chloropyridine,
3-amino-4-chloropyridine, and
2-amino-3-chloropyridine,
there are obtained:
(a) 6-phenyl-11H-pyrido[3,4-b][1,4]benzodiazepine,
(b) 10-phenyl-5H-pyrido[4,3-b][1,4]benzodiazepine, and
(c) 10-phenyl-5H-pyrido[3,2-b][1,4]benzodiazepine.

EXAMPLES 36a TO 36c

Following the procedure of Example 3, the following:
[2-[(4-amino-3-pyridinyl)amino]phenyl]methanone,
[2-[(3-amino-4-pyridinyl)amino]phenyl]methanone, and
[2-[(2-amino-3-pyridinyl)amino]phenyl]methanone,
are converted to:
(a) 6-phenyl-11H-pyrido[3,4-b][1,4]benzodiazepine,
(b) 10-phenyl-5H-pyrido[4,3-b][1,4]benzodiazepine, and
(c) 10-phenyl-5H-pyrido[3,2-b][1,4]benzodiazepine.

EXAMPLES 37a TO 37c

Following the procedure of Example 9 and substituting equal molar amounts of the following for 6-phenyl-11H-pyrido[2,3-b][1,4]benzodiazepine:
6-phenyl-11H-pyrido[3,4-b][1,4]benzodiazepine,
10-phenyl-5H-pyrido[4,3-b][1,4]benzodiazepine, and
10-phenyl-5H-pyrido[3,2-b][1,4]benzodiazepine,
there are obtained:
(a) N,N-dimethyl-6-phenyl-11H-pyrido[3,4-b][1,4]benzodiazepine-11-propanamine fumarate,
(b) N,N-dimethyl-10-phenyl-5H-pyrido[4,3-b][1,4]benzodiazepine-5-propanamine fumarate, and
(c) N,N-dimethyl-10-phenyl-5H-pyrido[3,2-b][1,4]benzodiazepine-5-propanamine fumarate.

EXAMPLE 38

5,6-Dihydro-6-phenyl-N-methyl-11H-pyrido[2,3-b][1,4]benzodiazepine-11-propanamine To a solution of 1.4 g (0.0035 mole) of N-[3-[6-phenyl)-11H-pyrido[2,3-b][1,4]benzodiazepine-11-yl]propyl]carbamic acid ethyl ester (from Example 29) in tetrahydrofuran under nitrogen gas was added 0.4 g (0.0105 mole) of lithium aluminum hydride and slight exothermic reaction occurred. The mixture was cooled to prevent overheating. The mixture was stirred at reflux temperature for 16 hr. Thin layer chromatography indicated only partial conversion had occurred. An additional 0.4 g (0.0105 mole) of lithium aluminum hydride was added and the mixture refluxed overnight. Thin-layer chromatography indicated the product was predominantly the title compound.

EXAMPLE 39

6-(2-Thienyl)-11H-pyrido[2,3-b][1,4]benzodiazepine

Following the procedure of Example 20, [2-[(3-amino-2-pyridinyl)amino]phenyl](2-thienyl)methanone is heated with para toluene sulfonic acid catalyst in organic solvent while removing water in a Dean-Stark trap to give the title compound.

EXAMPLE 40

6-(3-Thienyl)-11H-pyrido[2,3-b][1,4]benzodiazepine

Following the procedure of Example 20, [2-[(3-amino-2-pyridinyl)amino]phenyl](3-thienyl)methanone is heated with para toluene sulfonic acid catalyst in organic solvent while removing water in a Dean-Stark trap to give the title compound.

EXAMPLE 41

6-(2-Pyridinyl)-11H-pyrido[2,3-b][1,4]benzodiazepine

Following the procedure of Example 3, [2-[(3-amino-2-pyridinyl)amino]phenyl](2-pyridinyl)methanone is cyclized to the title compound.

EXAMPLE 42

6-(3-Pyridinyl)-11H-pyrido[2,3-b][1,4]benzodiazepine

Following the procedure of Example 3, [2-[(3-amino-2-pyridinyl)amino]phenyl](3-pyridinyl)methanone is cyclized to the title compound.

EXAMPLE 43

6-(4-Pyridinyl)-11H-pyrido[2,3-b][1,4]benzodiazepine

Following the procedure of Example 3, [2-[(3-amino-2-pyridinyl)amino]phenyl](4-pyridinyl)methanone is cyclized to the title compound.

EXAMPLE 44

N,N-Dimethyl-6-(2-thienyl)-11H-pyrido[2,3-b][1,4]benzodiazepine-11-propanamine

Following the procedure of Example 23, 6-(2-thienyl)11H-pyrido[2,3-b][1,4]benzodiazepine is reacted with sodium hydride followed by reaction with 3-dimethylaminopropyl chloride to give the title compound.

EXAMPLE 45

N,N-Dimethyl-6-(3-thienyl)-11H-pyrido[2,3-b][1,4]benzodiazepine-11-propanamine

Following the procedure of Example 23, 6-(3-thienyl)11H-pyrido[2,3-b][1,4]benzodiazepine is reacted with sodium hydride followed by reaction with 3-dimethylaminopropyl chloride to give the title compound.

EXAMPLE 46

N,N-Dimethyl-6-(2-pyridinyl)-11H-pyrido[2,3-b][1,4]benzodiazepine-11-propanamine Following the procedure of Example 23, 6-(2-pyridinyl)11H-pyrido[2,3-b][1,4]benzodiazepine is reacted with sodium hydride followed by reaction with 3-dimethylaminopropyl chloride to give the title compound.

EXAMPLE 47

N,N-Dimethyl-6-(3-pyridinyl)-11H-pyrido[2,3-b][1,4]benzodiazepine-11-propanamine Following the procedure of Example 23, 6-(3-pyridinyl)11H-pyrido[2,3-b][1,4]benzodiazepine is reacted with sodium hydride followed by reaction with 3-dimethylaminopropyl chloride to give the title compound.

EXAMPLE 48

N,N-Dimethyl-6-(4-pyridinyl)-11H-pyrido[2,3-b][1,4]benzodiazepine-11-propanamine Following the procedure of Example 23, 6-(4-pyridinyl)-11H-pyrido[2,3-b][1,4]benzodiazepine is reacted with sodium hydride followed by reaction with 3-dimethylaminopropyl chloride.

EXAMPLES 49a TO 49g

Following the procedure of Example 6, the following methanone compounds of Intermediate 15:
[2-[(3-amino-4-methyl-2-pyridinyl)amino]phenyl]-phenylmethanone,
[2-[(3-amino-5-methyl-2-pyridinyl)amino]phenyl]-phenylmethanone,
[2-[(3-amino-6-methyl-2-pyridinyl)amino]phenyl]-phenylmethanone,
[2-[(3-amino-5,6-dimethyl-2-pyridinyl)amino]phenyl]-phenylmethanone,
[2-[(3-amino-6-methoxy-2-pyridinyl)amino]phenyl]-phenylmethanone,
[2-[(3-amino-2-methyl-4-pyridinyl)amino]phenyl]-phenylmethanone, and
[2-[(3-amino-5-methoxy-2-pyridinyl)amino]phenyl]-phenylmethanone,
are converted to the following pyridobenzodiazepines:
(a) 4-methyl-6-phenyl-11H-pyrido[2,3-b][1,4]benzodiazepine,
(b) 3-methyl-6-phenyl-11H-pyrido[2,3-b][1,4]benzodiazepine,
(c) 2-methyl-6-phenyl-11H-pyrido[2,3-b][1,4]benzodiazepine,
(d) 2,3-dimethyl-6-phenyl-11H-pyrido[2,3-b][1,4]benzodiazepine,
(e) 2-methoxy-6-phenyl-11H-pyrido[2,3-b][1,4]benzodiazepine,
(f) 1-methyl-10-phenyl-5H-pyrido[4,3-b][1,4]benzodiazepine,
and
(g) 3-methoxy-6-phenyl-11H-pyrido[2,3-b][1,4]benzodiazepine.

EXAMPLES 50a TO 50g

Following the procedure of Example 23, the pyridobenzodiazepines prepared in Example 49 are reacted with sodium hydride and 3-dimethylaminopropyl chloride to give the following:
(a) N,N,4-trimethyl-6-phenyl-11H-pyrido[2,3-b][1,4]benzodiazepine-11-propanamine,
(b) N,N,3-trimethyl-6-phenyl-11H-pyrido[2,3-b][1,4]benzodiazepine-11-propanamine,
(c) N,N2-trimethyl-6-phenyl-11H-pyrido[2,3-b][1,4]benzodiazepine-11-propanamine, (d) N,N,2,3-tetramethyl-6-phenyl-11H-pyrido[2,3-b][1,4]benzodiazepine-11-propanamine,
(e) 2-methoxy-N,N-dimethyl-6-phenyl-11H-pyrido[2,3-b][1,4]benzodiazepine-11-propanamine,
(f) N,N,1-trimethyl-10-phenyl-5H-pyrido[4,3-b][1,4]benzodiazepine-5-propanamine, and
(g) 3-methoxy-N,N-dimethyl-6-phenyl-11H-pyrido[2,3-b][1,4]benzodiazepine-11-propanamine.

EXAMPLE 51a TO 51c

Following the procedure of Example 22 but substituting the following for [2-[(3-amino-2-pyridinyl)amino]phenyl](4-fluorophenyl)methanone:
[2-[(3-amino-2-pyridinyl)amino]phenyl](2-fluorophenyl)methanone,
[2-[(3-amino-2-pyridinyl)amino]phenyl](2-chlorophenyl)methanone, and
[2-[(3-amino-2-pyridinyl)amino]phenyl](2-bromophenyl)methanone,
there are obtained:
(a) 6-(2-fluorophenyl)-11H-pyrido[2,3-b][1,4]benzodiazepine,
(b) 6-(2-chlorophenyl)-11H-pyrido[2,3-b][1,4]benzodiazepine, and
(c) 6-(2-bromophenyl)-11H-pyrido[2,3-b][1,4]benzodiazepine.

EXAMPLES 52a TO 52c

Following the procedure of Example 23, substituting the following pyrido[1,4]benzodiazepines for 6-(4-fluorophenyl)-11H-pyrido[2,3-b][1,4]benzodiazepine:
6-(2-fluorophenyl)-11H-pyrido[2,3-b][1,4]benzodiazepine,
6-(2-chlorophenyl)-11H-pyrido[2,3-b][1,4]benzodiazepine,
6-(2-bromophenyl)-11H-pyrido[2,3-b][1,4]benzodiazepine,
there are obtained:
(a) 6-(2-fluorophenyl)-N,N-dimethyl-11H-pyrido[2,3-b][1,4]benzodiazepine-11-propanamine, m.p. 92°–94° C.; recrystallizing solvent isopropyl alcohol-isopropyl ether,
(b) 6-(2-chlorophenyl)-N,N-dimethyl-11H-pyrido[2,3][1,4]benzodiazepine-11-propanamine, m.p. 104°–105° C.; recrystallizing solvent: isopropyl ether, and
(c) 6-(2-bromophenyl)-N,N-dimethyl-11H-pyrido[2,3-b][1,4]benzodiazepine-11-propanamine, m.p. 96°–98° C.; recrystallizing solvent: isopropyl ether.

EXAMPLES 53a AND 53b

Following the procedure of Example 9, the following are substituted for 3-dimethylaminopropyl chloride:
3-dimethylamino-2-methylpropyl chloride, and
4-dimethylaminobutyl chloride,
there are obtained:
(a) N,N,β-trimethyl-6-phenyl-11H-pyrido[2,3-b][1,4]benzodiazepine-11-propanamine fumarate, and
(b) N,N-dimethyl-6-phenyl-11H-pyrido[2,3-b][1,4]benzodiazepine-11-butanamine fumarate.

EXAMPLES 54a AND 54b

When in the procedure of Example 11 the following are substituted for 4-(3-chlorophopyl)morpholine hydrochloride:
1-(3-chloropropyl)pyrrolidine hydrochloride, and
1-(3-chloropropyl)-4-methylpiperazine hydrochloride,
there are obtained:
6-phenyl-11-[3-(1-pyrrolidinyl)propyl]-11H-pyrido[2,3-b][1,4-benzodiazepine], and
6-phenyl-11-[3-(4-methyl-1-piperazinyl)propyl]-11H-pyrido[2,3-b][1,4]benzodiazepine.

EXAMPLES 55a TO 55c

When in the procedure of Example 9 the following are substituted for 6-phenyl-11H-pyrido[2,3-b][1,4]benzodiazepine:
8-methyl-6-phenyl-11H-pyrido[3,4-b][1,4]benzodiazepine,
6-(4-chlorophenyl)-11H-pyrido[3,4-b ][1,4]benzodiazepine, and
3-methoxy-6-phenyl-11H-pyrido[3,4-b][1,4]benzodiazepine,
there are obtained:
(a) N,N,8-trimethyl-6-phenyl-11H-pyrido[3,4-b][1,4]benzodiazepine-11-propanamine, and
(b) 6-(4-chlorophenyl)-N,N-dimethyl-11H-pyrido[3,4-b][1,4]benzodiazepine-11-propanamine, and
(c) 3-methoxy-N,N-dimethyl-6-phenyl-11H-pyrido[3,4-b][1,4]benzodiazepine-11-propanamine.

EXAMPLES 56a TO 56d

When in the procedure of Example 17 the following are substituted for 8-chloro-6-phenyl-11H-pyrido[2,3-b][1,4]benzodiazepine:
6-phenyl-11H-pyrido[2,3-b][1,4]benzodiazepine,
8-chloro-6-(2-nitrophenyl)-11H-pyrido[2,3-b][1,4]benzodiazepine,
8-chloro-6-(2-chlorophenyl)-11H-pyrido[2,3-b][1,4]benzodiazepine, and
8-chloro-6-(2-bromophenyl)-11H-pyrido[2,3-b][1,4]benzodiazepine,
there are obtained:
(a) 11-methyl-6-phenyl-11H-pyrido[2,3-b][1,4]benzodiazepine,
(b) 8-chloro-11-methyl-6-(2-nitrophenyl)-11H-pyrido[2,3-b][1,4]benzodiazepine, m.p. 165°–166° C., recrystallizing solvent: ethyl alcohol,
(c) 8-chloro-6-(2-chlorophenyl)-11-methyl-11H-pyrido[2,3-b][1,4]benzodiazepine, m.p. 150°–152° C., recrystallizing solvent: isopropyl alcohol-isopropyl ether, and
(d) 6-(2-bromophenyl)-8-chloro-11-methyl-11H-pyrido[2,3-b][1,4]benzodiazepine, m.p. 121°–123° C., recrystallizing solvent: isopropyl ether.

EXAMPLE 57

N-Methyl-N-[3-(11H-pyrido[2,3-b][1,4]benzodiazepine-11-yl)propyl]carbamic acid methyl ester The title compound is prepared by reacting 6-phenyl-11H-pyrido[2,3-b][1,4]benzodiazepine and (3-chloropropyl)methylcarbamic acid methyl ester.

EXAMPLE 58

9-Hydroxy-N,N-dimethyl-6-phenyl-11H-pyrido[2,3-b][1,4]benzodiazepine-11-propanamine The title compound is prepared by reacting 11-[3-(dimethylamino)propyl]-9-methoxy-6-phenyl-11H-pyrido[2,3-b][1,4]benzodiazepine with hydrogen iodide and glacial acetic acid.

EXAMPLE 59

3-Hydroxy-N,N-dimethyl-6-phenyl-11H-pyrido[2,3-b][1,4]benzodiazepine-11-propanamine The title compound is prepared by reacting 3-methoxy-N,N-dimethyl-6-phenyl-11H-pyrido[2,3-b][1,4]benzodiazepine-11-propanamine with hydrogen iodide and glacial acetic acid.

TABLE 2

| Example | R | Ar | Y | Z | n | Salt |
|---|---|---|---|---|---|---|
| 1 | H | $C_6H_5-$ | H | H | 0 | — |
| 2 | H | $C_6H_5$ | H | 8-Cl | 0 | — |
| 3 | H | $C_6H_5$ | H | 9-Cl | 0 | — |
| 4 | H | $2\text{-Cl}-C_6H_4-$ | H | 8-Cl | 1 | — |
| 5 | H | $4\text{-Cl}-C_6H_4$ | H | H | 0 | — |
| 6 | H | $4\text{-}CH_3-C_6H_4-$ | H | H | 0 | — |
| 7 | H | $4\text{-}OCH_3-C_6H_4-$ | H | H | 0 | — |
| 8 | $-(CH_2)_3-N(CH_3)_2$ | $C_6H_5-$ | H | 8-Cl | 0 | oxalate |
| 9 | $-(CH_2)_3-N(CH_3)_2$ | $C_6H_5-$ | H | H | 0 | fumarate |
| 10 | $-(CH_2)_2-N(CH_3)_2$ | $C_6H_5-$ | H | H | 0 | fumarate |
| 11 | $-(CH_2)_3-4\text{-morpholinyl}$ | $C_6H_5-$ | H | H | 0 | fumarate |
| 12 | $-(CH_2)_3-N(C_2H_5)_2$ | $C_6H_5-$ | H | H | 0 | oxalate |
| 13 | $-(CH_2)_3-N(CH_3)_2$ | $C_6H_5-$ | H | 9-Cl | 0 | fumarate |
| 14 | $-(CH_2)_3-1\text{-piperidinyl}$ | $C_6H_5-$ | H | H | 0 | fumarate |
| 15 | $-(CH_2)_3-N(CH_3)_2$ | $4\text{-Cl}-C_6H_4-$ | H | H | 0 | fumarate |
| 16 | $-(CH_2)_2-N(CH_3)_2$ | $C_6H_5-$ | H | 8-Cl | 0 | oxalate |
| 17 | $-CH_3$ | $C_6H_5-$ | H | 8-Cl | 0 | — |
| 18 | $-(CH_2)_3-N(CH_3)_2$ | $4\text{-}CH_3-C_6H_4-$ | H | H | 0 | fumarate |
| 19 | $-(CH_2)_3-N(CH_3)_2$ | $4\text{-}OCH_3-C_6H_4-$ | H | H | 0 | fumarate |
| 20 | H | $3\text{-Cl}-C_6H_4-$ | H | H | 0 | — |
| 21 | $-(CH_2)_3-N(CH_3)_2$ | $3\text{-Cl}-C_6H_4-$ | H | H | 0 | fumarate |
| 22 | H | $4\text{-F}-C_6H_4-$ | H | H | 0 | — |
| 23 | $-(CH_2)_3-N(CH_3)_2$ | $4\text{-F}-C_6H_4-$ | H | H | 0 | HCl, ½ $H_2O$ |
| 24 | $-(CH_2)_3-1\text{-phthalimido}$ | $C_6H_5-$ | H | H | 0 | — |
| 25 | $-(CH_2)_3-NH_2$ | $C_6H_5-$ | H | H | 0 | 2 HCl, 2 $H_2O$ |
| 26 | $-(CH_2)_3-NH_2$ | $C_6H_5-$ | H | H | 0 | — |
| 27 | $-(CH_2)_3-N=CH-OC_2H_5$ | $C_6H_5-$ | H | H | 0 | — |
| 28 | $-(CH_2)_3-NHCH_3$ | $C_6H_5-$ | H | H | 0 | 2 HCl |
| 29 | $-(CH_2)_3-NHC(O)-OC_2H_5$ | $C_6H_5-$ | H | H | 0 | — |
| 30 | $-(CH_2)_3-N(CH_3)_2$ | $C_6H_5-$ | H | H | 1 | 2 HCl, 0.5 $H_2O$ |
| 31(a) | H | $4\text{-}C_2H_5-C_6H_4-$ | H | H | 0 | — |
| (b) | H | $4\text{-}i\text{-}C_3H_7-C_6H_4-$ | H | H | 0 | — |
| (c) | H | $4\text{-Br}-C_6H_4-$ | H | H | 0 | — |
| (d) | H | $4\text{-F}-C_6H_4-$ | H | H | 0 | — |
| (e) | H | $4\text{-}OC_2H_5-C_6H_4-$ | H | H | 0 | — |
| (f) | H | $4\text{-}NO_2-C_6H_4-$ | H | H | 0 | — |
| (g) | H | $4\text{-}CF_3-C_6H_4-$ | H | H | 0 | — |
| (h) | H | $4\text{-}CH_3-C_6H_4-$ | H | H | 0 | — |
| (i) | H | $3\text{-}C_2H_5-C_6H_4-$ | H | H | 0 | — |
| (j) | H | $3\text{-}OCH_3-C_6H_4-$ | H | H | 0 | — |
| (k) | H | $3\text{-}OC_2H_5-C_6H_4-$ | H | H | 0 | — |
| (l) | H | $2\text{-}NO_2-C_6H_4-$ | H | H | 0 | — |
| (m) | H | $3\text{-}CF_3-C_6H_4-$ | H | H | 0 | — |
| (n) | H | $2\text{-}CH_3-C_6H_4-$ | H | H | 0 | — |
| (o) | H | $2\text{-}C_2H_5-C_6H_4-$ | H | H | 0 | — |
| (p) | H | $2\text{-}OCH_3-C_6H_4$ | H | H | 0 | — |
| (q) | H | $2,4(Cl)_2-C_6H_3-$ | H | H | 0 | — |
| (r) | H | $3,4,5\text{-}(OCH_3)_3-C_6H_2-$ | H | H | 0 | — |
| 32(a) | H | $C_6H_5-$ | H | 8-Cl | 0 | — |
| (b) | H | $C_6H_5-$ | H | 7-Cl | 0 | — |
| (c) | H | $C_6H_5-$ | H | 9-Br | 0 | — |
| (d) | H | $C_6H_5-$ | H | 9-F | 0 | — |
| (e) | H | $C_6H_5-$ | H | $9\text{-}CF_3$ | 0 | — |

TABLE 2-continued

| Example | R | Ar | Y | Z | n | Salt |
|---|---|---|---|---|---|---|
| (f) | H | C₆H₅— | H | 9-CH₃ | 0 | — |
| (g) | H | C₆H₅— | H | 8-CH₃ | 0 | — |
| (h) | H | C₆H₅— | H | 7-CH₃ | 0 | — |
| (i) | H | C₆H₅— | H | 9-C₂H₅ | 0 | — |
| (j) | H | C₆H₅— | H | 9-OCH₃ | 0 | — |
| (k) | H | C₆H₅— | H | 9-OC₂H₅ | 0 | — |
| (l) | H | C₆H₅— | H | 9-NO₂ | 0 | — |
| (m) | H | C₆H₅— | H | 8-NO₂ | 0 | — |
| (n) | H | C₆H₅— | H | 10-CH₃ | 0 | — |
| (o) | H | C₆H₅— | H | 10-Cl | 0 | — |
| 33(a) | —(CH₂)₃—N(CH₃)₂ | 4-C₂H₅—C₆H₄— | H | H | 0 | — |
| (b) | —(CH₂)₃—N(CH₃)₂ | 4-i-C₃H₇—C₆H₄— | H | H | 0 | — |
| (c) | —(CH₂)₃—N(CH₃)₂ | 4-Br—C₆H₄— | H | H | 0 | — |
| (d) | —(CH₂)₃—N(CH₃)₂ | 4-F—C₆H₄— | H | H | 0 | — |
| (e) | —(CH₂)₃—N(CH₃)₂ | 4-OC₂H₅—C₆H₄— | H | H | 0 | — |
| (f) | —(CH₂)₃—N(CH₃)₂ | 4-NO₂—C₆H₄— | H | H | 0 | — |
| (g) | —(CH₂)₃—N(CH₃)₂ | 4-CF₃—C₆H₄— | H | H | 0 | — |
| (h) | —(CH₂)₃—N(CH₃)₂ | 3-CH₃—C₆H₄— | H | H | 0 | — |
| (i) | —(CH₂)₃—N(CH₃)₂ | 3-C₂H₅—C₆H₄— | H | H | 0 | — |
| (j) | —(CH₂)₃—N(CH₃)₂ | 3-OCH₃—C₆H₄— | H | H | 0 | — |
| (k) | —(CH₂)₃—N(CH₃)₂ | 3-OC₂H₅—C₆H₄— | H | H | 0 | — |
| (l) | —(CH₂)₃—N(CH₃)₂ | 2-NO₂—C₆H₄— | H | H | 0 | — |
| (m) | —(CH₂)₃—N(CH₃)₂ | 3-CF₃—C₆H₄— | H | H | 0 | — |
| (n) | —(CH₂)₃—N(CH₃)₂ | 2-CH₃—C₆H₄— | H | H | 0 | — |
| (o) | —(CH₂)₃—N(CH₃)₂ | 2-C₂H₅—C₆H₄— | H | H | 0 | — |
| (p) | —(CH₂)₃—N(CH₃)₂ | 2-OCH₃—C₆H₄— | H | H | 0 | — |
| (q) | —(CH₂)₃—N(CH₃)₂ | 2,4-(Cl)₂—C₆H₃— | H | H | 0 | — |
| (r) | —(CH₂)₃—N(CH₃)₂ | 3,4,5-(OCH₃)₃—C₆H₂ | H | H | 0 | — |
| 34(a) | —(CH₂)₃—N(CH₃)₂ | C₆H₅— | H | 8-Cl | 0 | — |
| (b) | —(CH₂)₃—N(CH₃)₂ | C₆H₅— | H | 7-Cl | 0 | — |
| (c) | —(CH₂)₃—N(CH₃)₂ | C₆H₅— | H | 9-Br | 0 | — |
| (d) | —(CH₂)₃—N(CH₃)₂ | C₆H₅— | H | 9-F | 0 | — |
| (e) | —(CH₂)₃—N(CH₃)₂ | C₆H₅— | H | 9-CF₃ | 0 | — |
| (f) | —(CH₂)₃—N(CH₃)₂ | C₆H₅— | H | 9-CH₃ | 0 | — |
| (g) | —(CH₂)₃—N(CH₃)₂ | C₆H₅— | H | 8-CH₃ | 0 | — |
| (h) | —(CH₂)₃—N(CH₃)₂ | C₆H₅— | H | 7-CH₃ | 0 | — |
| (i) | —(CH₂)₃—N(CH₃)₂ | C₆H₅— | H | 9-C₂H₅ | 0 | — |
| (j) | —(CH₂)₃—N(CH₃)₂ | C₆H₅— | H | 9-OCH₃ | 0 | — |
| (k) | —(CH₂)₃—N(CH₃)₂ | C₆H₅— | H | 9-OC₂H₅ | 0 | — |
| (l) | —(CH₂)₃—N(CH₃)₂ | C₆H₅— | H | 9-NO₂ | 0 | — |
| (m) | —(CH₂)₃—N(CH₃)₂ | C₆H₅— | H | 8-NO₂ | 0 | — |
| (n) | —(CH₂)₃—N(CH₃)₂ | C₆H₅— | H | 10-CH₃ | 0 | — |
| (o) | —(CH₂)₃—N(CH₃)₂ | C₆H₅— | H | 10-Cl | 0 | — |
| 38 | —(CH₂)₃NHCH₃ | C₆H₅— | H | H | 1 | — |
| 39 | H | 2-thienyl | H | H | 0 | — |
| 40 | H | 3-thienyl | H | H | 0 | — |
| 41 | H | 2-pyridinyl | H | H | 0 | — |
| 42 | H | 3-pyridinyl | H | H | 0 | — |
| 43 | H | 4-pyridinyl | H | H | 0 | — |
| 44 | —(CH₂)₃—N(CH₃)₂ | 2-thienyl | H | H | 0 | — |
| 45 | —(CH₂)₃—N(CH₃)₂ | 3-thienyl | H | H | 0 | — |
| 46 | —(CH₂)₃—N(CH₃)₂ | 2-pyridinyl | H | H | 0 | — |
| 47 | —(CH₂)₃—N(CH₃)₂ | 3-pyridinyl | H | H | 0 | — |
| 48 | —(CH₂)₃—N(CH₃)₂ | 4-pyridinyl | H | H | 0 | — |
| 49(a) | H | C₆H₅— | 4-CH₃ | H | 0 | — |
| (b) | H | C₆H₅— | 3-CH₃ | H | 0 | — |
| (c) | H | C₆H₅— | 2-CH₃ | H | 0 | — |
| (d) | H | C₆H₅— | 2,3-(CH₃)₂ | H | | |
| (e) | H | C₆H₅— | 2-OCH₃ | H | 0 | — |
| (g) | H | C₆H₅— | 3-OCH₃ | H | 0 | — |
| 50(a) | —(CH₂)₃—N(CH₃)₂ | C₆H₅— | 4-CH₃ | H | 0 | — |
| (b) | —(CH₂)₃—N(CH₃)₂ | C₆H₅— | 3-CH₃ | H | 0 | — |
| (c) | —(CH₂)₃—N(CH₃)₂ | C₆H₅— | 2-CH₃ | H | 0 | — |
| (d) | —(CH₂)₃—N(CH₃)₂ | C₆H₅— | 2,3-(CH₃)₂ | H | 0 | — |
| (e) | —(CH₂)₃—N(CH₃)₂ | C₆H₅— | 2-OCH₃ | H | 0 | — |
| (g) | —(CH₂)₃—N(CH₃)₂ | C₆H₅— | 3-OCH₃ | H | 0 | — |
| 51(a) | H | 2-F—C₆H₅— | H | H | 0 | — |
| (b) | H | 2-Cl—C₆H₄— | H | H | 0 | — |
| (c) | H | 2-Br—C₆H₄— | H | H | 0 | — |
| 52(a) | —(CH₂)₃—N(CH₃)₂ | 2-F—C₆H₄— | H | H | 0 | — |
| (b) | —(CH₂)₃—N(CH₃)₂ | 2-Cl—C₆H₄— | H | H | 0 | — |
| (c) | —(CH₂)₃—N(CH₃)₂ | 2-Br—C₆H₄— | H | H | 0 | — |
| 53(a) | —CH₂CH(CH₃)CH₂—N(CH₃)₂ | C₆H₅— | H | H | 0 | fumarate |
| (b) | —(CH₂)₄—N(CH₃)₂ | C₆H₅— | H | H | 0 | fumarate |
| 54(a) | —(CH₂)₃—1-pyrrolidinyl | C₆H₅— | H | H | 0 | — |
| (b) | —(CH₂)₃—4-methylpiperazin- | C₆H₅— | H | H | 0 | — |

TABLE 2-continued

| Example | R | Ar | Y | Z | n | Salt |
|---|---|---|---|---|---|---|
| | 1-yl | | | | | |
| 56(a) | —$CH_3$ | $C_6H_5$— | H | H | 0 | — |
| (b) | —$CH_3$ | 2-$NO_2$—$C_6H_4$— | H | 8-Cl | 0 | — |
| (c) | —$CH_3$ | 2-Cl—$C_6H_4$— | H | 8-Cl | 0 | — |
| (d) | —$CH_3$ | 2-Br—$C_6H_4$— | H | 8-Cl | 0 | — |
| 57 | —$(CH_2)_3$—N($CH_3$)—C(O)O$CH_3$ | $C_6H_5$— | H | H | 0 | — |
| 58 | —$(CH_2)_3$—N($CH_3$)$_2$ | $C_6H_5$— | H | 9-OH | 0 | — |
| 59 | —$(CH_2)_3$—N($CH_3$)$_2$ | $C_6H_5$— | 3-OH | H | 0 | — |

[Chemical structure diagram]

| Example | R | Ar | Y | Z | n | Salt |
|---|---|---|---|---|---|---|
| 35(a) | H | $C_6H_5$— | H | H | 0 | — |
| 36(a) | H | $C_6H_5$— | H | H | 0 | — |
| 37(a) | —$(CH_2)_3$—N($CH_3$)$_2$ | $C_6H_5$— | H | H | 0 | fumarate |
| 55(a) | —$(CH_2)_3$—N($CH_3$)$_2$ | $C_6H_5$— | H | 8-$CH_3$ | 0 | — |
| (b) | —$(CH_2)_3$—N($CH_3$)$_2$ | $C_6H_5$— | 3-$OCH_3$ | H | 0 | — |
| (c) | —$(CH_2)_3$—N($CH_3$)$_2$ | $C_6H_5$— | H | H | 0 | — |

[Chemical structure diagram]

| Example | R | Ar | Y | Z | n | Salt |
|---|---|---|---|---|---|---|
| 35(b) | H | $C_6H_5$— | H | H | 0 | — |
| 36(b) | H | $C_6H_5$— | H | H | 0 | — |
| 37(b) | —$(CH_2)_2$N($CH_3$)$_2$ | $C_6H_5$— | H | H | 0 | fumarate |
| 49(f) | H | $C_6H_5$— | 1-$CH_3$ | H | 0 | — |
| 50(f) | —$(CH_2)_3$—N($CH_3$)$_2$ | $C_6H_5$— | 1-$CH_3$ | H | 0 | — |

[Chemical structure diagram]

| Example | R | Ar | Y | Z | n | Salt |
|---|---|---|---|---|---|---|
| 35(c) | H | $C_6H_5$— | H | H | 0 | — |
| 36(c) | H | $C_6H_5$— | H | H | 0 | — |
| 37(c) | —$(CH_2)_3$—N($CH_3$)$_2$ | $C_6H_5$— | H | H | 0 | fumarate |

FORMULATION AND ADMINISTRATION

Effective quantities of the foregoing pharmacologically active compounds of Formula Ip or Formula II may be administered to humans for therapeutic purposes according to usual modes of administration and in usual forms, such as orally in solutions, emulsions, suspensions, pills, tablets and capsules, in pharmaceutically acceptable carriers and parenterally in the form of sterile solutions.

Exemplary of solid carriers for oral administration are such as lactose, magnesium, stearate, terra alba, sucrose, talc, stearic acid, gelatin, agar, pectin or acacia.

Exemplary of liquid carriers for oral administration are vegetable oils and water.

For intramuscular administration the carrier or excipient may be a sterile, parenterally acceptable liquid; e.g., water or a parenterally acceptable oil; e.g., arachis oil contained in ampules.

Although very small quantities of the active materials of the present invention are effective when minor therapy is involved or in cases of administration to subjects having a relatively low body weight, unit dosages are usually from five milligrams or above and preferably 10, 25, 50, or 100 milligrams or even higher, preferably administered three or four times per day, depending, of course, upon the emergency of the situation, the compound used, and the particular result desired. Twenty-five to 200 milligrams appears optimum per unit dose or usual broader ranges appear to be about 10 to 500 milligrams per unit dose. Daily dosages usually required should range from about 0.3 to about 20 mg/kg/day, preferably 0.3 to 10 mg/kg for the more active compounds. The active ingredients of the invention may be combined with other compatible pharmacologically active agents. It is only necessary that the active ingredient constitute an effective amount; i.e., such that a suitable effective dosage will be obtained consistent with the dosage form employed. Obviously, several unit dosage forms may be administered at about the same time. The exact individual dosages as well as daily dosages will, of course, be determined according to standard medical principles under the direction of a physician.

The following formulations are representative for the pharmacologically active compounds of this invention.

FORMULATIONS

1. Capsules

Capsules of 10 mg and 50 mg of active ingredient per capsule are prepared. With the higher amounts of active ingredient, reduction may be made in the amount of lactose.

| Typical blend for encapsulation | 10 mg. Per Capsule | 50 mg. Per Capsule |
|---|---|---|
| Active ingredient, as salt | 10 | 50 |
| Lactose | 259 | 219 |
| Starch | 126 | 126 |
| Magnesium stearate | 4 | 4 |
| Total | 399 | 399 |

Additional capsule formulations preferably contain a higher dosage of active ingredient and are as follows:

| Ingredients | 100 mg. per Capsule | 250 mg. per Capsule | 500 mg. per Capsule |
|---|---|---|---|
| Active ingredient, as salt | 100 | 250 | 500 |
| Lactose | 214 | 163 | 95 |
| Starch | 87 | 81 | 47 |
| Magnesium stearate | 4 | 6 | 8 |
| Total | 399 | 500 | 650 |

In each case, uniformly blend the selected active ingredient with lactose, starch, and magnesium stearate and encapsulate the blend.

2. Tablets

A typical formulation for a tablet containing 5.0 mg of active ingredient per tablet follows. The formulation may be used for other strengths of active ingredient by adjustment of weight of dicalcium phosphate.

| | Per Tablet, mg. |
|---|---|
| 1. Active ingredient | 10.0 |
| 2. Corn starch | 15.0 |
| 3. Corn starch (paste) | 12.0 |
| 4. Lactose | 35.0 |
| 5. Dicalcium phosphate | 132.0 |
| 6. Calcium stearate | 2.0 |
| Total | 202.0 |

Uniformly blend 1, 2, 4 and 5. Prepare 3 as a 10 percent paste in water. Granulate the blend with starch paste and pass the wet mass through an 8 mesh screen. The wet granulation is dried and sized through a 12 mesh screen. The dried granules are blended with the calcium stearate and compressed.

| 3. Injectable - 2% sterile solution | Per cc |
|---|---|
| Active ingredient mg. | 20 |
| Preservative, e.g., chlorobutanol, w/vol. percent | 0.5 |
| Water for injection q.s. | |

Prepare solution, clarify by filtration, fill into vials, seals and autoclave.

Various modifications and equivalents will be apparent to one skilled in the art and may be made in the compounds, compositions and methods of the present invention without departing from the spirit and scope thereof, and it is therefore understood that the invention is to be limited only by the scope of the appended claims.

What is claimed is:

1. A compound selected from the group having the formula:

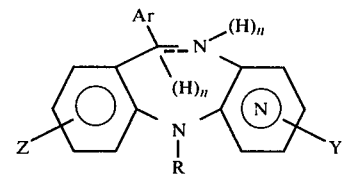

wherein:
R is —alk$^1$—N—R$^1$R$^2$;
R$^1$ and R$^2$ are selected from the group consisting of hydrogen and loweralkyl;
Ar is selected from the group consisting of 2, 3 or 4-pyridinyl, 2 or 3-thienyl, phenyl or phenyl substituted by 1 to 3 radicals selected from halogen, loweralkyl, loweralkoxy, trifluoromethyl or nitro and may be the same or different;
alk$^1$ is a straight or branched hydrocarbon chain of 1–8 carbon atoms;
Z is selected from the group consisting of hydrogen, halogen, loweralkyl, loweralkoxy, hydroxy or nitro;
Y is selected from the group consisting of hydrogen or 1–2 radicals selected from loweralkyl, loweralkoxy or hydroxy and may be the same or different;
n is 0 or 1 and when n is zero the dotted line is a double bond, and the pharmaceutically acceptable acid addition salts thereof.

2. The compound of claim 1 which is 8-chloro-N,N-dimethyl-6-phenyl-11H-pyrido[2,3-b][1,4]benzodiazepine-11-propanamine.

3. The compound of claim 1 which is 8-chloro-N,N-dimethyl-6-phenyl-11H-pyrido[2,3-b][1,4]benzodiazepine-11-propanamine oxalate [1:1].

4. The compound of claim 1 which is N,N-dimethyl-6-phenyl-11H-pyrido[2,3-b][1,4]benzodiazepine-11-propanamine.

5. The compound of claim 1 which is N,N-dimethyl-6-phenyl-11H-pyrido[2,3-b][1,4]benzodiazepine-11-propanamine fumarate [1:1].

6. The compound of claim 1 which is N,N-dimethyl-6-phenyl-11H-pyrido[2,3-b][1,4]benzodiazepine-11-ethanamine.

7. The compound of claim 1 which is N,N-dimethyl-6-phenyl-11H-pyrido[2,3-b][1,4]benzodiazepine-11-ethanamine fumarate [1:1].

8. The compound of claim 1 which is N,N-diethyl-6-phenyl-11H-pyrido[2,3-b][1,4]benzodiazepine-11-propanamine.

9. The compound of claim 1 which is N,N-diethyl-6-phenyl-11H-pyrido[2,3-b][1,4]benzodiazepine-11-propanamine oxalate [1:1].

10. The compound of claim 1 which is 9-chloro-N,N-dimethyl-6-phenyl-11H-pyrido[2,3-b][1,4]benzodiazepine-11-propanamine.

11. The compound of claim 1 which is 9-chloro-N,N-dimethyl-6-phenyl-11H-pyrido[2,3-b][1,4]-benzodiazepine-11-propanamine fumarate [1:1].

12. The compound of claim 1 which is 6-(4-chlorophenyl)-N,N-dimethyl-11H-pyrido[2,3-b][1,4]benzodiazepine-11-propanamine.

13. The compound of claim 1 which is 6-(4-chlorophenyl)-N,N-dimethyl-11H-pyrido[2,3-b][1,4]benzodiazepine-11-propanamine fumarate [1:1].

14. The compound of claim 1 which is 8-chloro-N,N-dimethyl-6-phenyl-11H-pyrido[2,3-b][1,4]benzodiazepine-11-ethanamine.

15. The compound of claim 1 which is 8-chloro-N,N-dimethyl-6-phenyl-11H-pyrido[2,3-b][1,4]benzodiazepine-11-ethanamine oxalate [1:1].

16. The compound of claim 1 which is N,N-dimethyl-6-(4-methylphenyl)-11H-pyrido[2,3-b][1,4]benzodiazepine-11-propanamine.

17. The compound of claim 1 which is N,N-dimethyl-6-(4-methylphenyl)-11H-pyrido[2,3-b][1,4]benzodiazepine-11-propanamine fumarate [1:1].

18. The compound of claim 1 which is 6-(4-methoxyphenyl)-N,N-dimethyl-11H-pyrido[2,3-b][1,4]benzodiazepine-11-propanamine.

19. The compound of claim 1 which is 6-(4-methoxyphenyl)-N,N-dimethyl-11H-pyrido[2,3-b][1,4]benzodiazepine-11-propanamine fumarate [1:1].

20. The compound of claim 1 which is 6-(3-chlorophenyl)-N,N-dimethyl-11H-pyrido[2,3-b][1,4]benzodiazepine-11-propanamine.

21. The compound of claim 1 which is 6-(4-fluorophenyl)-N,N-dimethyl-11H-pyrido[2,3-b][1,4]benzodiazepine-11-propanamine.

22. The compound of claim 1 which is 6-phenyl-11H-pyrido[2,3-b][1,4]benzodiazepine-11-propanamine.

23. The compound of claim 1 which is 6-phenyl-11H-pyrido[2,3-b][1,4]benzodiazepine-11-propanamine dihydrochloride hemihydrate.

24. The compound of claim 1 which is N-methyl-6-phenyl-11H-pyrido[2,3-b][1,4]benzodiazepine-11-propanamine.

25. The compound of claim 1 which is N-methyl-6-phenyl-11H-pyrido[2,3-b][1,4]benzodiazepine-11-propanamine dihydrochloride.

26. The compound of claim 1 which is 5,6-dihydro-N,N-dimethyl-6-phenyl-11H-pyrido[2,3-b][1,4]benzodiazepine-11-propanamine.

27. The compound of claim 1 which is 5,6-dihydro-N,N-dimethyl-6-phenyl-11H-pyrido[2,3-b][1,4]benzodiazepine-11-propanamine, dihydrochloride hemihydrate.

28. The compound of claim 1 which is 5,6-dihydro-N-methyl-6-phenyl-11H-pyrido[2,3-b][1,4]benzodiazepine-11-propanamine.

29. The compound of claim 1 which is 6-(2-fluorophenyl)-N,N-dimethyl-11H-pyrido[2,3-b][1,4]benzodiazepine-11-propanamine.

30. The compound of claim 1 which is 6-(2-chlorophenyl)-N,N-dimethyl-11H-pyrido[2,3-b][1,4]benzodiazepine-11-propanamine.

31. The compound of claim 1 which is 6-(2-bromophenyl)-N,N-dimethyl-11H-pyrido[2,3-b][1,4]benzodiazepine-11-propanamine.

32. The compound of claim 1 which is 6-(3-chlorophenyl)-N,N-dimethyl-11H-pyrido[2,3-b][1,4]benzodiazepine-11-propanamine fumarate [1:1].

33. The compound of claim 1 which is 6-(4-fluorophenyl)-N,N-dimethyl-11H-pyrido[2,3-b][1,4]benzodiazepine-11-propanamine hydrochloride hemihydrate.

34. The compound of claim 1 which is 6-(2-fluorophenyl)-N-methyl-11H-pyrido[2,3-b][1,4]benzodiazepine-11-propanamine or a pharmaceutically acceptable acid addition salt thereof.

* * * * *